(12) United States Patent
Gebert-Schwarzwaelder et al.

(10) Patent No.: US 10,617,618 B2
(45) Date of Patent: Apr. 14, 2020

(54) AGENT FOR OXIDATIVE DYEING OF HAIR CONTAINING ANISOLE DERIVATIVES

(71) Applicant: Henkel AG & Co. KGaA, Duesseldorf (DE)

(72) Inventors: Antje Gebert-Schwarzwaelder, Neuss (DE); Ralph Nemitz, Juechen (DE); Astrid Kroos, Monheim (DE); Annika Koenen, Grevenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/204,170

(22) Filed: Nov. 29, 2018

(65) Prior Publication Data

US 2019/0167551 A1    Jun. 6, 2019

(30) Foreign Application Priority Data

Dec. 6, 2017    (DE) .................. 10 2017 222 001

(51) Int. Cl.
| | | |
|---|---|---|
| *A61K 8/41* | (2006.01) | |
| *A61K 8/34* | (2006.01) | |
| *A61K 8/49* | (2006.01) | |
| *A61Q 5/10* | (2006.01) | |

(52) U.S. Cl.
CPC .............. *A61K 8/411* (2013.01); *A61K 8/347* (2013.01); *A61K 8/415* (2013.01); *A61K 8/4926* (2013.01); *A61Q 5/10* (2013.01); *A61K 2800/4324* (2013.01)

(58) Field of Classification Search
CPC ........ A61K 8/347; A61K 8/411; A61K 8/415; A61K 8/4926; A61K 2800/4324; A61Q 5/10
See application file for complete search history.

(56) References Cited

U.S. PATENT DOCUMENTS

| | | | |
|---|---|---|---|
| 2015/0366771 A1 | 12/2015 | Sabelle | |
| 2015/0374601 A1* | 12/2015 | Sabelle | ............... A61K 8/31 8/409 |

FOREIGN PATENT DOCUMENTS

WO    2006029712 A1    3/2006

OTHER PUBLICATIONS

Kh. Schrader, Grundlagen and Rezepturen der Kosmetika, 2. Auflage, Hüthig Buch Verlag, Heidelberg, 1989.

* cited by examiner

*Primary Examiner* — Yanzhi Zhang
(74) *Attorney, Agent, or Firm* — Lorenz & Kopf, LLP

(57) ABSTRACT

The present disclosure relates to agents for the oxidative coloring of keratinic fibers, which are characterized in hat they contain derivatives of anisole as novel developer molecules.

9 Claims, No Drawings

AGENT FOR OXIDATIVE DYEING OF HAIR CONTAINING ANISOLE DERIVATIVES

CROSS-REFERENCE TO RELATED APPLICATION

This application claims priority to German Patent Application No. 10 2017 222 001.5, filed Dec. 6, 2017, which is incorporated herein by reference in its entirety.

TECHNICAL FIELD

The present disclosure relates to agents for th oxidative coloring of keratinic fibers, which are characterized in that they contain derivatives of anisole as novel developer molecules.

BACKGROUND

Changing the shape and color of hair represents an important area of modern cosmetics. The consumer uses color-changing agents for the fashionable color design of hairstyles or for the lamination of gray or white hair with fashionable or natural shades.

The person skilled in the art knows various systems for providing color-changing cosmetic agents, in particular for the skin or keratinic fibers such as human hair, depending on the requirements of the coloring or color change.

So-called oxidation colorants are used for permanent, intensive colorings with corresponding fastness properties. Such colorants usually contain oxidation dye precursors, so-called developer components and coupler components. The developer components form the actual dyes under the influence of oxidizing agents or of atmospheric oxygen with each another or with coupling with one or more coupler components. The oxidation colorants are characterized by intensive excellent, long-lasting dyeing results. A mixture of a larger number of oxidation dye precursors can be used for natural-looking colorings, wherein in many cases, further direct dyes are additionally used for shading.

In particular, oxidative hair colorants are often disadvantageous for the user despite their advantageous dyeing properties, so that there is constant need for further development for oxidation dye precursors.

Many compounds have been explored in the search for oxidation dye precursors having a good compatibility profile, but they often suffer from application problems, in particular lack of gray coverage. Moreover, in spite of already highly developed dyeing systems, there is still a need for dyeing systems which achieve excellent brilliance and intensity of coloring, but simultaneously have very good durability, very good fastness properties and excellent homogeneity.

There is a need for improvement in particular in the generation of highly up-to-date shades in the natural shade field.

Many known dyeing systems with which natural shades can be achieved have no satisfactory wash fastness and their skin compatibility is often unsatisfactory.

BRIEF SUMMARY

In an exemplary embodiment, an agent is provided for dyeing keratinic fibers. An exemplary agent includes, in a cosmetic carrier, at least one compound of the formula (I) and/or a physiologically compatible salt of a compound of the formula (I),

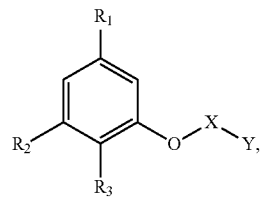
(I)

in which
$R_1$, $R_3$ independently of one another stand for a hydroxyl group or amino group, wherein the amino group may be substituted by a group Q,
$R_2$ stands for a hydroxy group or an amino group, wherein the amino group may be substituted by a group Q,
Q stands for an alkyl group or an aryl group,
X stands for a $C_1$-$C_6$ alkyl group or a group of the general formula (II),

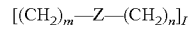
$[(CH_2)_m—Z—(CH_2)_n]_I$ (II)

Z stands for an oxygen atom or an amino group,
m stands for a number from 1 to 3,
n stands for a number from 0 to 3,
I stands for a number from 1 to 3, and
Y stands for a hydrogen atom, a hydroxy group, an alkoxy group or an amino group, wherein the amino group may be substituted with one or two Q groups and Y stands for a hydrogen atom when n=0.

In another embodiment, a method is provided for dyeing keratinic fibers. The method includes applying an agent to the keratinic fibers. In the exemplary embodiment, the agent includes, in a cosmetic carrier, at least one compound of the formula (I) and/or a physiologically compatible salt of a compound of the formula (I),

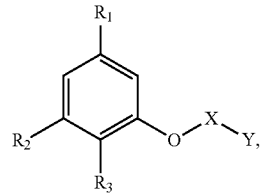
(I)

in which
$R_1$, $R_3$ independently of one another stand for a hydroxyl group or amino group, wherein the amino group may be substituted by a group Q,
$R_2$ stands for a hydroxy group or an amino group, wherein the amino group may be substituted by a group Q,
Q stands for an alkyl group or an aryl group,
X stands for a $C_1$-$C_6$ alkyl group or a group of the general formula (II),

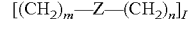
$[(CH_2)_m—Z—(CH_2)_n]_I$ (II)

Z stands for an oxygen atom or an amino group,
m stands for a number from 1 to 3,
n stands for a number from 0 to 3,
I stands for a number from 1 to 3, and
Y stands for a hydrogen atom, a hydroxy group, an alkoxy group or an amino group, wherein the amino group may be substituted with one or two Q groups and Y stands for a hydrogen atom when n=0.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is therefore to lower the abovementioned disadvantages of known oxidative hair colorants. The colorants should produce intense colorings with high color and good resistance to external influences, in particular with good lightfastness and wash fastness, which suffer no color attenuation or color shift even after repeated shampooing of the hair. In addition, the colorings should have the least selectivity as possible, that is, to achieve, as much as possible, even and uniform dyeing results on differently pretreated hair. In addition, the colorants should have a toxicologically advantageous profile.

Another object of the present disclosure is to develop oxidation dye precursors with which, in particular, natural shades can be achieved, which have excellent wash fastness and a good skin compatibility profile.

Finally, it is desirable to achieve the greatest possible nuance of the individual shades.

It has been found that, as oxidation dye precursors, certain alkoxylated anisole derivatives are outstandingly suitable for dyeing keratinic fibers. They give colorations with good fastness properties, high color intensity and excellent brilliance, and excellent gray coverage.

A first subject of the present disclosure is an agent for dyeing keratinic fibers, in particular human hair, which contains, in a cosmetic carrier, at least one anisole derivative of the general formula (I),

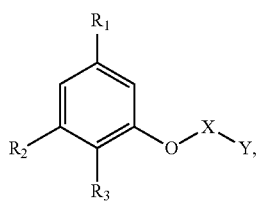

(I)

in which
  $R_1$, $R_3$ independently of one another stand for a hydroxyl group or amino group, wherein the amino group may be substituted by a group Q,
  $R_2$ stands for a hydroxy group or an amino group, wherein the amino group may be substituted by a group Q,
  Q stands for an alkyl group or an aryl group,
  X stands for a $C_1$-$C_6$ alkyl group or a group of the general formula (II), $$[(CH_2)_m\text{—}Z\text{—}(CH_2)_n]_i \quad \text{(II)}$$

Z stands for an oxygen atom or an amino group,
  m stands for a number between from about 1 and about 3
  n stands for a number between from about 0 and about 3,
  i stands for a number between from about 1 and about 3,
  Y stands for a hydrogen atom, a hydroxy group, an alkoxy group or an amino group, wherein the amino group may be substituted by one or two Q groups. Y must stand for a hydrogen atom when n=0.

These show particularly appealing shades in the natural shade field and good wash fastness.

In an exemplary embodiment, the radicals $R^1$ and $R^3$ of the general formula (I) stand for an amino group. In addition, in an exemplary embodiment, Z is an oxygen atom. Furthermore, in an exemplary embodiment, m, n and i are 1 or 2 independently of each other.

Thus, the agents for keratin fibers, in particular human hairs, belong to a particular exemplary embodiment which, in a cosmetically acceptable carrier, contains at least one compound selected from the group formed from:

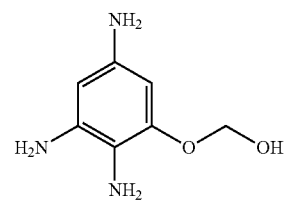

2-(2,3,5-triaminophenoxy) methanol

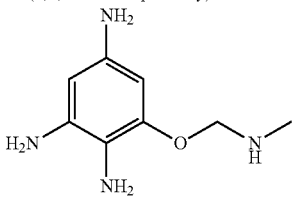

6-(methylaminomethoxy) benzene-1,2,4-triamine

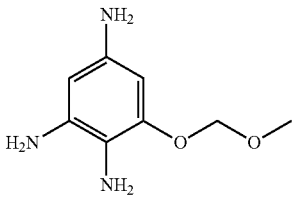

6-(methoxymethoxy) benzene-1,2,4-triamine

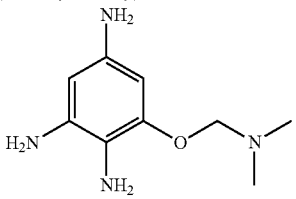

6-[(dimethylamino)methoxy] benzene-1,2,4-triamine

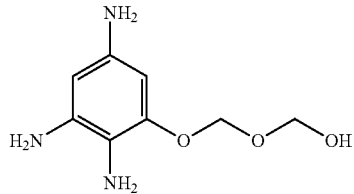

(2,3,5-triaminophenoxy) methoxymethanol

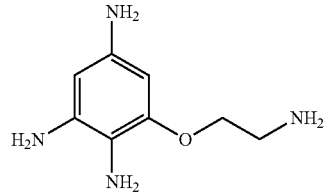

6-(2-aminoethoxy) benzene-1,2,4-triamine

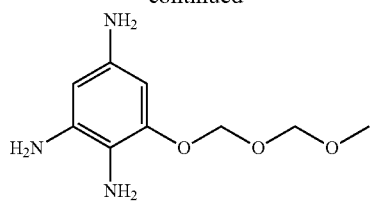

6-(methoxymethoxymethoxy) benzene-1,2,4-triamine

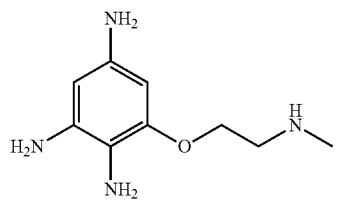

6-[2-(methylamino)ethoxy] benzene-1,2,4-triamine

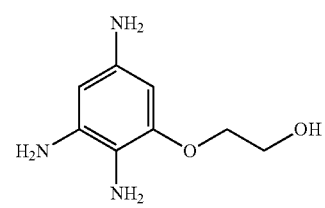

2-(2,3,5-triaminophenoxy) ethanol

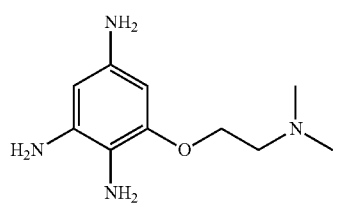

6-[2-(dimethylamino)ethoxy] benzene-1,2,4-triamine

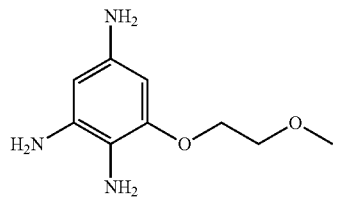

6-(2-methoxyethoxy) benzene-1,2,4-triamine

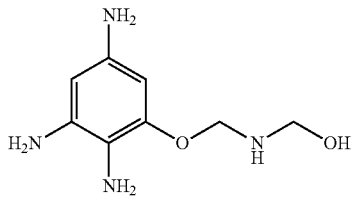

[(2,3,5-triaminophenoxy) methylamino] methanol

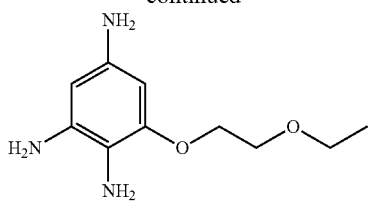

6-(2-ethoxyethoxy) benzene-1,2,4-triamine

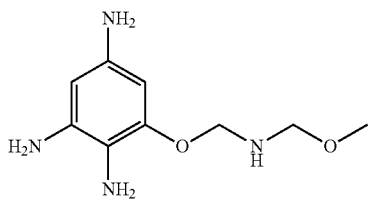

6-[(methoxymethylamino)methoxy] benzene-1,2,4-triamine

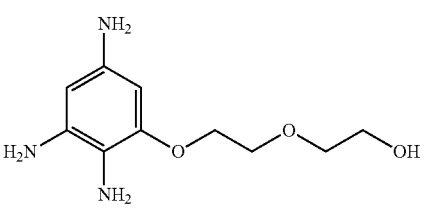

2-[2-(2,3,5-triaminophenoxy)ethoxy] ethanol

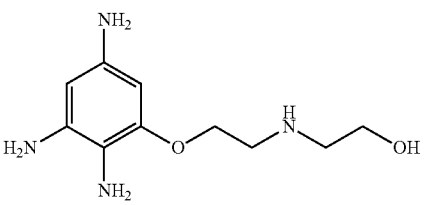

2-[2-(2,3,5-triaminophenoxy)ethylamino] ethanol

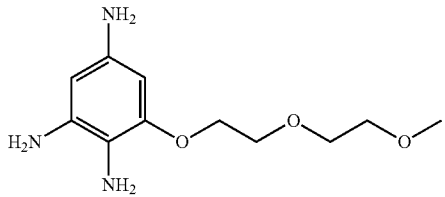

6-[2-(2-methoxyethoxy)ethoxy] benzene-1,2,4-triamine

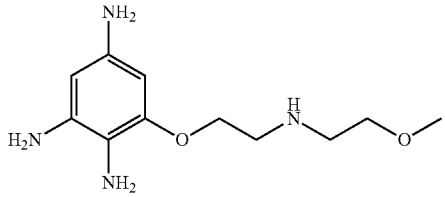

6-[2-(2-methoxyethylamino) ethoxy] benzene-1,2,4-triamine

-continued

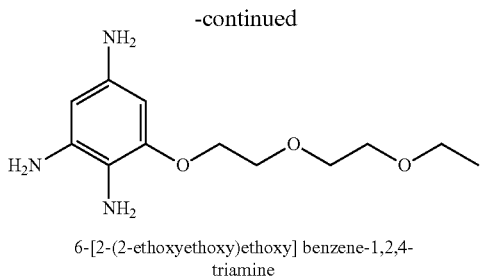

6-[2-(2-ethoxyethoxy)ethoxy] benzene-1,2,4-triamine and from the mixtures and/or physiologically compatible salts of these compounds.

In the course of work leading to this present disclosure, it has been found that it is particularly advantageous when the radicals $R_1$, $R_2$ and $R_3$ each stand for an $NH_2$ group. To the same extent, it may be particularly preferred that Y stands for an $NH_2$ group and/or that Z is an oxygen atom.

These dyes are particularly well tolerated by the skin and can be used for the production of a variety of natural shades with very good wash fastness.

A further exemplary embodiment of the first subject of the present disclosure is characterized in that the agent contains at least one compound according to formula (I), which may be selected from 6-(methoxymethoxy) benzene-1,2,4-triamine, 6-(2-methoxyethoxy) benzene-1,2,4-triamine and 6-[2-(2-ethoxyethoxy)ethoxy] benzene-1,2,4-triamine, their mixtures and/or physiologically compatible salts.

The compounds according to formula (I) are derivatives of anisole and thus amino compounds. The known acid addition salts can be prepared in a conventional manner from these. All statements of this document and accordingly the scope claimed therefore relate both to the compounds present in free form and to their physiologically compatible salts of organic or inorganic acids. Examples of such salts are the hydrochlorides, hydrobromides, sulfates, phosphates, acetates, propionates, citrates and lactates. The hydrochlorides and the sulfates may be particularly preferred. in certain embodiments, very particular preference is given to the monohydrochlorides, the dihydrochlorides and the trihydrochlorides.

Wool, furs, feathers and in particular human hair are understood to mean keratinic fibers. In principle, however, the colorants as contemplated herein can also be used for dyeing other natural fibers, such as cotton, jute, sisal, linen or silk, modified natural fibers, such as regenerated cellulose, nitro-, alkyl- or hydroxyalkyl- or acetylcellulose.

The agents as contemplated herein contain the compounds of the formula (I) in a cosmetic carrier, preferably in a suitable aqueous, alcoholic or aqueous-alcoholic carrier. For the purpose of hair coloring, such carriers are, for example, creams, emulsions, gels or surfactant-containing foaming solutions, such as shampoos, foam aerosols, foam formulations or other preparations which are suitable for use on the hair. However, it is also conceivable to integrate the compounds according to the formula (I) in a powder-form or tablet-form formulation.

For the purposes of the present disclosure, aqueous-alcoholic solutions are understood to mean aqueous solutions containing from about 3 to about 70% by weight of a $C_1$-$C_4$ alcohol, in particular ethanol or isopropanol. The agents as contemplated herein may additionally contain further organic solvents, such as methoxybutanol, benzyl alcohol, ethyl diglycol or 1,2-propylene glycol. Preference is given to all water-soluble organic solvents.

Examples of a $C_1$-$C_8$ alkyl group are the groups methyl, ethyl, propyl, isopropyl, n-butyl, s-butyl and t-butyl, n-pentyl, i-pentyl, i-hexyl, n-hexyl, i-heptyl, n-heptyl, i-octyl and n-octyl. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a $C_2$-$C_6$ hydroxyalkyl group are a hydroxymethyl group, a 2-hydroxyethyl group, a 2-hydroxypropyl group, a 3-hydroxypropyl group, a 4-hydroxybutyl group, a 5-hydroxypentyl and a 6-hydroxyhexyl group; a 2-hydroxyethyl group is particularly preferred. $C_1$-$C_6$ alkoxy groups preferred as contemplated herein are the methoxy, ethoxy or propoxy group. Examples of a $C_2$-$C_8$ polyhydroxyalkyl group are the 2,3-dihydroxypropyl group, 3,4-dihydroxybutyl group and the 2,4-dihydroxybutyl group. The 2-methoxyethyl group, 2-ethoxyethyl group, 3-methoxypropyl group and 3-ethoxypropyl group are examples of a $C_2$-$C_6$-alkoxy-$C_2$-$C_6$ alkyl group, preferred are the 2-methoxyethyl group and 2-ethoxyethyl group. Preferred examples of a $C_1$-$C_6$-alkoxy-$C_2$-$C_6$ hydroxyalkyl group are the groups methoxymethanol, methoxyethanol, methoxypropan-1-ol, methoxybutan-1-ol, 2-ethoxymethanol, 2-ethoxyethanol, 2-ethoxypropanel-ol or 4-ethoxybutan-1-ol. Preferred examples of $C_1$-$C_6$ polyalkoxy groups as contemplated herein are the (methoxymethoxy) methoxy group, the 2-(2-methoxyethoxy) ethoxy group, the 3-(3-methoxypropoxy) propoxy group, the (ethoxymethoxy) methoxy group, the 2-(2-ethoxyethoxy) ethoxy group and the 3-(3-ethoxypropoxy) propoxy group. Exemplary of an amino $C_2$-$C_6$ alkyl group are the methylamino, ethylamino and propylamino groups. Examples of a $C_1$-$C_6$ alkylamino (C $C_6$) alkoxy group are a [(methoxymethyl)amino]methyl group, a 2-[(2-methoxyethyl)amino] ethyl group, a [(2-ethoxyethyl)amino] ethyl group or a 3-[(3-methoxypropyl)amino] propyl group. Preferred examples of $C_1$-$C_6$-alkylamino-(C $C_6$) alkyl groups are the (methylamino) methyl group, the (methylamino) ethyl group, the (methylamino) propyl group, the (methylamino) butyl group, the (ethylamino) methyl group, the (ethylamino) ethyl group or the (ethylamino) propyl group. Preferred examples of a nitro-($C_1$-$C_6$)-alkyl group are nitromethyl group, the 2-nitroethyl group, the 3-nitropropyl group and the 4-nitrobutyl group. Preferred examples of a cyano-$C_1$-$C_6$ alkyl group are a cyanomethyl and a 2-cyanoethyl group. Exemplary of a $C_1$-$C_6$-alkylamido-$C_1$-$C_6$ alkyl group are the N-methyl-2-acetamide group, the N,N-dimethyl-2-acetamide group, the N-ethyl-2-acetamide group, the N,N-diethyl-2-acetamide group, the N-methyl-3-propanamide group, the N-diethyl-3-propanamide group. Preferred examples of aryl groups are phenyl, toluyl and benzyl. Preferred halogen-($C_1$-$C_6$)-alkyl groups are the 2-chloroethyl group, the 3-chloropropyl group, the 2-bromoethyl group and the 3-bromopropyl group.

Agents preferred as contemplated herein are characterized in that they contain the compounds according to the formula (I), their mixture and/or their physiologically tolerable salts in a proportion by weight of from about 0.001 to about 5.0% by weight, preferably from about 0.025 to about 2.5% by weight, particularly preferably from about 0.05 to about 2.0% by weight and very particularly preferably from about 0.1 to about 1.5% by weight, based on the total weight of the ready-to-use agent.

The compounds of the formula (I) can be present as sole, color-changing compounds in the agent as contemplated herein. However, it is preferred as contemplated herein when the agent additionally contains at least one oxidation dye precursor of the type of a coupler component.

Coupler components do not form significant coloring as part of the oxidative coloring alone, but always require the presence of developer components.

Coupler components as contemplated herein allow at least one substitution of a chemical radical of the coupler by the oxidized form of the developer component. Covalent bonds are formed between the coupler component and the developer component.

Coupler components as contemplated herein are preferably selected as at least one compound from one of the following classes:
  m-aminophenol and/or its derivatives,
  m-diaminobenzene and/or its derivatives,
  o-diaminobenzene and/or its derivatives,
  o-aminophenol derivatives, such as o-aminophenol,
  naphthalene derivatives having at least one hydroxy group,
  di- or trihydroxybenzene and/or derivatives thereof,
  pyridine derivatives,
  pyrimidine derivatives,
  monohydroxyindole derivatives and/or monoamine indole derivatives,
  monohydroxyindoline derivatives and/or monoaminoindoline derivatives,
  pyrazolone derivatives such as 1-phenyl-3-methylpyrazol-5-one,
  morpholine derivatives such as 6-hydroxybenzomorpholine or 6-aminobenzomorpholine,
  quinoxaline derivatives such as 6-methyl-1,2,3,4-tetrahydroquinoxaline,
mixtures of two or more compounds from one or more of these classes are also within the scope of this embodiment as contemplated herein.

Particularly preferred coupler components as contemplated herein are selected from 3-amino-phenol, 5-amino-2-methylphenol, 3-amino-2-chloro-6-methylphenol, 2-hydroxy-4-amino-phenoxy ethanol, 5-amino-4-chloro-2-methylphenol, 5-(2-hydroxyethyl)-amino-2-methylphenol, 2,4-di-chloro-3-aminophenol, 2-aminophenol, 3-phenylenediamine, 2-(2,4-diaminophenoxy) ethanol, 1,3-bis (2,4-di-aminophenoxy) propane, 1-methoxy-2-amino-4-(2-hydroxyethylamino) benzene, 1,3-bis(2,4-diaminophenyl) propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-4,5-dimethylphenyl}amino) ethanol, 2-[3-morpholin-4-ylphenyl)amino] ethanol, 3-amino-4-(2-methoxyethoxy)-5-methylphenylamine, 1-amino-3-bis-(2-hydroxyethyl) aminobenzene, 5-amino-4-chloro-o-cresol, 3-amino-6-methoxy-2-methylaminopyridine, 5-amino-4-chloro-o-cresol, resorcinol, 2-methylresorcinol, 4-chlororesorcinol, 1,2,4-tri-hydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1 J-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically compatible salts of the aforementioned compounds.

Particularly preferred coupler components are 1,3-bis-(2,4-diaminophenoxy) propane, m-aminophenol, resorcinol, 5-amino-2-methylphenol, 2-methylresorcinol, 2-chloro-6-methyl-3-aminophenol, 2,7-dihydroxynaphthalene, 4-chlororesorcinol, 2,6-dihydroxy-3,4-dimethylpyridine, 1-amino-3-bis-(2-hydroxyethyl) aminobenzene (Lehmann's blue), 2,4-diaminophenoxyethanol, 5-amino-4-chloro-o-cresol, 3-amino-6-methoxy-2-methylaminopyridine, 5-amino-4-chloro-o-cresol and/or a physiologically compatible salt of these compounds.

The coupler components are preferably used in the agents as contemplated herein in an amount of from about 0.001 to about 5.0% by weight, more preferably from about 0.025 to about 2.5% by weight, particularly preferably from about 0.05 to about 2% by weight and in particular from about 0.1 to about 1.5% by weight, each based on the total weight of the ready-to-use agent.

It may also be advantageous as contemplated herein to use a physiologically compatible salt of this compound instead of the uncharged compound in the above preferred combinations of oxidation dye precursors.

In order to achieve a balanced and subtle nuance formation, it is advantageous as contemplated herein when further coloring components are contained in the agent as contemplated herein.

It may therefore be preferred as contemplated herein when the agent contains at least one further coloring component which is selected from additional oxidation dye precursors of the developer type and/or direct dyes.

In addition to the developer type oxidation dye precursors according to formula (I), the agents of the present disclosure may additionally contain at least one further developer component.

Preferred further developer components are selected from at least one compound from the group formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazole)-1-yl)propyl] amine, N,N'-bis-(2-hydroxyethyl)-N,N'-bis-(4-aminophenyl)-1,3-diamino-propan-2-ol, bis-(2-hydroxy-5-aminophenyl) methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl) phenol and 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, and the physiologically compatible salts of these compounds. Particularly preferred additional developer components are p-toluenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl] amine, and/or 4,5-diamino-1-(2-hydroxyethyl) pyrazole and their physiologically compatible salts.

The additional developer components are preferably used in an amount of from about 0.0001 to about 10% by weight, preferably from about 0.001 to about 5% by weight, each based on the ready-to-use agent.

Furthermore, the agents as contemplated herein may contain at least one direct dye. These are dyes that are absorbed directly onto the hair and do not require an oxidative process to form the color. Direct dyes are usually nitrophenylenediamines, nitroaminophenols, azo dyes, anthraquinones or indophenols.

The direct dyes are each used preferably in an amount of from about 0.001 to about 20% by weight, in particular from about 0.05 to about 5% by weight, each based on the total application preparation. The total amount of direct dyes is preferably at most about 3% by weight.

Direct dyes may be subdivided into anionic, cationic and nonionic direct dyes which are selected and used by those skilled in the art for the requirements of the carrier base.

Preferred anionic direct dyes are those compounds known under the international designations or trade names bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 and Yellow 87, Basic Orange 31 and Basic Red 51.

Nitro and quinone dyes and neutral azo dyes are in particular suitable nonionic direct dyes. Preferred nonionic direct dyes are those known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 and 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)-amino-4,6-dinitrophenol, 4-[(2-hydroxyethyl)-amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitro-phenol.

The agents as contemplated herein may also contain naturally-analogous dyes in addition to the compound according to the formula (I). Compositions as contemplated herein which contain precursors of naturally-analogous dyes are preferably used as air-oxidative colorants. Said compositions are consequently not added with an additional oxidizing agent in this embodiment.

The dye precursors of naturally-analogous dyes are each preferably used in an amount of from about 0.001 to about 5% by weight, based on the total application preparation. Especially suitable as precursors of natural-analogous hair dyes are derivatives of 5,6-dihydroxyindoline, in particular 5,6-dihydroxyindoline, N-methyl-5,6-dihydroxyindoline, N-ethyl-5,6-dihydroxyindoline, N-propyl-5,6,-dihydroxyindoline, N-butyl-5,6-dihydroxyindoline and 5,6-dihydroxyindoline-2-carboxylic acid, and also derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, and physiologically compatible salts of the above-mentioned compounds.

The development of the color can in principle be done with atmospheric oxygen in the case of oxidative colorings. Preferably, however, a chemical oxidizing agent is used, in particular if, in addition to the coloring, a lightening effect on human hair is desired. This lightening effect may be desired regardless of the staining method. Persulfates, peroxodisulfates, chlorites, hypochlorites and in particular hydrogen peroxide or and/or one of its solid addition products of organic or inorganic compounds are oxidation agents.

In order to prevent a premature, undesired reaction of the oxidation dye precursors by the oxidizing agent, oxidation dye precursors and oxidizing agents themselves are expediently prepared separately from each other and brought into contact only immediately before use.

In a further embodiment of the present disclosure, therefore, agents are preferred, which are characterized in that they are prepared immediately before use by mixing at least two preparations, wherein the at least two preparations are provided in at least two separately assembled containers and wherein one container contains a colorant (A) which contains, in a cosmetic carrier, at least one oxidation dye precursor according to formula (I), and a further container contains an oxidation agent preparation (B) containing at least one oxidizing agent.

The oxidizing agent preparation (B) preferably contains as the oxidizing agent hydrogen peroxide and/or one of its solid addition products of organic or inorganic compounds, such as urea, melamine and sodium borate.

Preferably, the amount of oxidizing agent in the ready-to-use agent is from about 0.5 to about 12% by weight, preferably from about 2 to about 10% by weight, more preferably from about 3 to about 6% by weight (calculated as about 100% $H_2O_2$), in each case based on the ready-to-use agent.

In a further preferred embodiment, the agent as contemplated herein is an agent for dyeing and, optionally, simultaneous lightening of keratinic fibers, which preferably contains from about 0.5 to about 15% by weight, preferably from about 1 to about 12.5% by weight, particularly preferably from about 1.5 to about 10% by weight and in particular from about 2 to about 6% by weight hydrogen peroxide, each based on the total weight of the ready-to-use agent.

Such oxidizing agent preparations are preferably aqueous, flowable oxidizing agent preparations. Preferred preparations are characterized in that the flowable oxidizing agent preparation, based on its weight, contains from about 40 to about 90% by weight, preferably from about 50 to about 85% by weight, particularly preferably from about 55 to about 80% by weight, more preferably from about 60 to about 77.5% by weight and in particular from about 65 to about 75% by weight of water.

According to the present disclosure, however, the oxidative colorant can also be applied to the hair together with a catalyst which activates the oxidation of the dye precursors. Such catalysts are, for example, certain enzymes, iodides, quinones or metal ions.

Furthermore, it has proven to be advantageous when the oxidizing agent preparations contain at least one stabilizer or complexing agent. Typical complexing agents and stabilizers which are preferred for the purposes of the present disclosure are, for example, polyoxycarboxylic acids, polyamines, ethylenediaminetetraacetic acid (EDTA), N-hydroxyethylethylenediaminetriacetic acid, diethylenetriaminepentaacetic acid (DTPA), ethylenediamine disuccinic acid (EDDS), hydroxyethyliminodiacetic acid, nitridodiacetic acid-3-propionic acid, isoserinediacetic acid, N,N-di-(2-hydroxyethyl)glycine, N-(1,2-dicarboxy-2-hydroxyethyl) glycine, N-(1,2-dicarboxy-2-hydroxyethyl) aspartic acid or nitrilotriacetic acid (NTA), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), diaminoalkyldi-(sulfosuccinic acid) (DDS), ethylenedicysteic acid (EDC), ethylenediamine-N-N'-bis (ortho-hydroxyphenyl) acetic acid (EDDHA), N-2-hydroxyethylamine-N,N-diacetic acid, glyceryl-iminodiacetic acid, iminodiacetic acid-N-2-hydroxypropylsulfonic acid, aspartic acid-N-carboxymethyl-N-2,5-hydroxypropyl-3-sulfonic acid, β-alanine-N,N-diacetic acid, aspartic acid-N,N'-diacetic acid, aspartic acid-N-monoacetic acid, dipicolinic acid, and their salts and/or derivatives, geminal diphosphonic acids such as 1-hydroxyethane-1,1-diphosphonic acid (HEDP), whose higher homologues having up to 8 carbon atoms and hydroxyl- or amino-containing derivatives thereof and 1-aminoethane-1,1-diphosphonic acid, whose higher homologues having up to 8 carbon atoms and derivatives containing hydroxy or amino groups, aminophosphonic acids such as ethylenediaminetetra (methylenephosphonic acid) (EDTMP), diethylenetriaminepenta(methylenephosphonic acid) (DTPMP) and their higher homologs, or nitrilo-tri (methylenephosphonic acid), phosphonopolycarboxylic acids such as 2-phosphonobutane-1,2,4-tri-carboxylic acid, cyclodextrins, and alkali stannates (sodium stannate), alkali pyrophosphates (tetra-sodium pyrophosphate, disodium pyrophosphate), alkali phosphates (sodium phosphate), and phosphoric acid and salts thereof.

These complexing agents are at least partially present as anions at the alkaline pH values of the treatment solutions required as contemplated herein. It is immaterial whether they are introduced in the form of acids or in the form of salts. Alkali, ammonium or alkylammonium salts, in particular sodium salts, are preferred in the case of use as salts.

Preferred complexing agents as contemplated herein are nitrogen-containing polycarboxylic acids, in particular EDTA, and phosphonates, preferably hydroxyalkane or aminoalkane phosphonates, and in particular 1-hydroxyethane-1,1-diphosphonate (HEDP) or its di- or tetrasodium salt and/or ethylenediamine tetramethylenephosphonate (EDTMP) or its hexasodium salt and/or diethylentriaminpentamethylenphosphonat (DTPMP) or its hepta- or octosodium salt.

The dyeing preparation and optionally oxidizing agent preparation contain other auxiliaries and additives. Thus, it has proved to be preferred as contemplated herein when the dyeing preparation and/or the oxidizing agent preparation contains at least one thickening agent. There are no fundamental restrictions with regard to these thickening agents. Both organic and purely inorganic thickening agents can be used.

According to a first preferred embodiment, the thickening agent is an anionic synthetic polymer. Preferred anionic groups are the carboxylate and sulfonate groups.

Examples of anionic monomers from which the polymeric anionic thickening agents may consist are acrylic acid, methacrylic acid, crotonic acid, itaconic acid, maleic anhydride and 2-acrylamido-2-methylpropanesulfonic acid. The acidic groups may be wholly or partly present as a sodium, potassium, ammonium, mono- or triethanolammonium salt. Preferred monomers are maleic anhydride and in particular 2-acrylamido-2-methylpropanesulfonic acid and acrylic acid.

Preferred anionic homopolymers are uncrosslinked and crosslinked polyacrylic acids. Allyl ethers of pentaerythritol, sucrose and propylene may be preferred crosslinking agents. Such compounds are, for example, commercially available under the trademark Carbopol®. Also preferred is the homopolymer of 2-acrylamido-2-methyl propane sulfonic acid, which is commercially available, for example, under the name Rheothik® 1 1 -80.

Within this first embodiment, it may further be preferred to use copolymers of at least one anionic monomer and at least one nonionic monomer. With regard to the anionic monomers, reference is made to the substances listed above. Preferred nonionic monomers are acrylamide, methacrylamide, acrylic acid esters, methacrylic acid esters, itaconic acid mono- and diesters, vinylpyrrolidinone, vinyl ethers and vinyl esters.

The anionic acrylic acid and/or methacrylic acid polymerizates or copolymerizates are preferably present in the agents as contemplated herein in an amount of from about 0.1 to about 10% by weight, particularly preferably from about 1 to about 5% by weight, based in each case on the weight of the agent.

Preferred anionic copolymers are, for example, copolymers of acrylic acid, methacrylic acid or their $C_1$-$C_6$ alkyl esters, as sold under the INCI declaration Acrylates Copolymers. An exemplary commercial product is, for example, Aculyn® 33 from Rohm & Haas. But also preferred are copolymers of acrylic acid, methacrylic acid or their $C_1$-$C_6$ alkyl esters and the esters of an ethylenically unsaturated acid and an alkoxylated fatty alcohol. Suitable ethylenically unsaturated acids are, in particular, acrylic acid, methacrylic acid and itaconic acid; suitable alkoxylated fatty alcohols are in particular steareth-20 or ceteth-20. Such copolymers are sold by Rohm & Haas under the trade name Aculyn® 22 and by National Starch under the trade names Structure® 2001 and Structure® 3011.

Preferred anionic copolymers are also acrylic acid-acrylamide copolymers and in particular polyacrylamide copolymers having monomers containing sulfonic acid groups. A particularly preferred anionic copolymer of from about 70 to about 55 mol % of acrylamide and from about 30 to about 45 mol % of 2-acrylamido-2-methylpropanesulfonic acid, wherein the sulfonic acid group is wholly or partly present as a sodium, potassium, ammonium, mono- or triethanolammonium salt. This copolymer may also be crosslinked, wherein crosslinking agents, preferably polyolefinically unsaturated compounds such as tetraallyloxythane, allylsucrose, allylpentaerythritol and methylene-bisacrylamide, are used. Such a polymer is contained in the commercial products Sepigel® 305 and Simulgel® 600 from SEPPIC. The use of these compounds, which in addition to the polymer component, contain a hydrocarbon mixture ($C$-$l_3$-$C$-$l_4$ isoparaffin or isohexadecan) and a non-ionic emulsifier (laureth-7 or polysorbate-80), has proved in the context of the present disclosure as particularly advantageous.

Polymers of maleic anhydride and methyl vinyl ether, in particular such with crosslinking, are preferred thickening agents. A maleic acid-methyl vinyl ether copolymer crosslinked with 1,9-decadiene is commercially available under the name Stabileze® QM.

The agent as contemplated herein may additionally contain at least one anionic acrylic acid and/or methacrylic acid polymerisate or copolymerisate.

Preferred polymerisates of this type are known:
polymerisates, for example, of at least about 10% by weight of acrylic acid lower alkyl ester, from about 25 to about 70% by weight of methacrylic acid and optionally up to about 40% by weight of a further comonomer,
mixed polymerisates of from about 50 to about 75% by weight ethyl acrylate, from about 25 to about 35% by weight of acrylic acid and from about 0 to about 25% by weight of other comonomers. Suitable dispersions of this type are commercially available, for example, under the trade name Latekoll® D (BASF).

Copolymerisates of from about 50 to about 60% by weight of ethyl acrylate, from about 30 to about 40% by weight of methacrylic acid and from about 5 to about 15% by weight of acrylic acid, crosslinked with ethylene glycol dimethacrylate.

According to another embodiment, the thickening agent is a cationic synthetic polymer. Preferred cationic groups are quaternary ammonium groups. In particular, those polymers in which the quaternary ammonium group are bonded via a C C$_4$ hydrocarbon group to a polymer main chain constructed from acrylic acid, methacrylic acid or derivatives thereof have proven to be particularly suitable.

Homopolymers of the General Formula (HP-1),

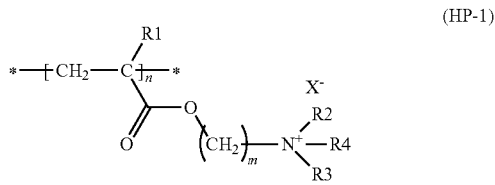

in which R1 is —H or —CH$_3$, R2, R3 and R4 independently of one another are selected from C$_1$-C$_4$ alkyl, alkenyl or hydroxyalkyl groups, m=1, 2, 3 or 4, n is a natural number and X$^-$ is a physiologically compatible organic or inorganic anion, and copolymers including essentially of the monomer units listed in formula (HP-1) and nonionic monomer units, are particularly preferred cationic polymeric gelling agents. Within the context of these polymers, preference is given to those as contemplated herein for which at least one of the following conditions applies:

R1 stands for a methyl group
R2, R3 and R4 stand for methyl groups
m has the value 2, suitable physiologically tolerated counterions X$^-$ include, for example, halide ions, sulfate ions, phosphate ions, methosulfate ions and organic ions such as lactate, citrate, tartrate and acetate ions. Preference is given to halide ions, in particular chloride.

A particularly suitable homopolymer is, if desired, crosslinked, poly(methacryloxy-ethyltrimethylammonium chloride) having the INCI name Polyquaternium-37. If desired, the crosslinking can be carried out with the aid of multiple olefinically unsaturated compounds, for example, divinylbenzene, tetraallyloxyethane, methylene bisacrylamide, diallyl ether, polyallyl polyglyceryl ethers, or allyl ethers of sugars or sugar derivatives such as erythritol, pentaerythritol, arabitol, mannitol, sorbitol, sucrose or glucose. Methylenebisacrylamide is an exemplary crosslinking agent.

The homopolymer is preferably used in the form of a non-aqueous polymer dispersion, which should have a polymer content of not less than about 30% by weight. Such polymer dispersions are commercially available under the names Salcare® SC 95 (about 50% polymer content, further component: mineral oil (INCI name: Mineral Oil) and tridecyl polyoxypropylene polyoxyethylene ether (INCI name: PPG-1-Trideceth-6)) and Salcare® SC 96 (about 50% polymer content, further components: mixture of diesters of propylene glycol with a mixture of caprylic and capric acid (INCI name: Propylene glycol dicaprylate/dicaprate) and tridecyl-polyoxy-propylene-polyoxyethylene ether (INCI name: PPG-1-Trideceth-6).

Copolymers having monomer units according to the formula (HP-1) preferably contain acrylamide, methacrylamide, acrylic acid-C C$_4$-alkyl esters and methacrylic acid-C C$_4$-alkyl esters as nonionic monomer units. The acrylamide is particularly preferred among these nonionic monomers. These copolymers can also be crosslinked, as described above in the case of the homopolymers. An exemplary copolymer as contemplated herein is the crosslinked acrylamide-methacroyl-oxyethyltrimethylammonium chloride copolymer. Such copolymers, in which the monomers are present in a weight ratio of about 20:80, are commercially available as about 50% non-aqueous polymer dispersion under the name Salcare® SC 92.

In a further preferred embodiment, naturally occurring thickening agents are used. Preferred thickening agents of this embodiment are, for example, nonionic guar gum. According to the present disclosure, both modified and unmodified guar gums can be used. Unmodified guar gums are sold under the trade name Jaguar® C from Rhone Poulenc. Modified guar gums preferred as contemplated herein contain C C$_6$-hydroxyalkyl groups. The groups are preferably hydroxymethyl, hydroxyethyl, hydroxypropyl and hydroxybutyl. Such modified guar gums are known in the art and can be prepared, for example, by reaction of the guar gums with alkylene oxides. The degree of hydroxyalkylation, which corresponds to the number of alkylene oxide molecules consumed in relation to the number of guar gum free hydroxy groups, is preferably between from about 0.4 and about 1.2. Such modified guar gums are commercially available under the trade names Jaguar® HP8, Jaguar® HP60, Jaguar® HP120, Jaguar® DC 293 and Jaguar® HP105 from Rhone Poulenc.

Further suitable natural thickening agents are also already known from the prior art.

Also preferred according to this embodiment are biosaccharide gums of microbial origin, such as scleroglucan gums or xanthan gums, gums from plant exudates such as gum arabic, ghatti gum, karaya gum, gum tragacanth, carrageenan gum, agar, locust bean gum, pectins, alginates, starch fractions and derivatives such as amylose, amylopectin and dextrins, cellulose derivatives such as methylcellulose, carboxyalkylcelluloses and hydroxyalkylcelluloses.

Preferred hydroxyalkylcelluloses are, in particular, the hydroxyethylcelluloses which are sold under the names Cellosize® from Amerchol and Natrosol® from Hercules. Suitable carboxyalkylcelluloses are, in particular, the carboxymethylcelluloses as are sold under the names Blanose® from Aqualon, Aquasorb® and Ambergum® from Hercules and Cellgon® from Montello.

Starch and its derivatives are also preferred. Starch is a storage material of plants, which occurs mainly in tubers and roots, in grain seeds and in fruits and can be obtained from a variety of plants in high yield. The polysaccharide, which is insoluble in cold water and forms a colloidal solution in boiling water may be, for example, obtained from potatoes, manioc, sweet potatoes, maranta, maize, cereals, rice, legumes such as peas and beans, bananas or the pulp of certain types of palms (for example, the sago palm). Natural, plant-derived starches and/or chemically or physically modified starches can be used as contemplated herein. Modification can be achieved, for example, by introducing different functional groups on one or more of the hydroxyl groups of the starch. Usually, they are esters, ethers or amides of starch with optionally substituted C C$_{40}$ radicals. Especially advantageous is a corn starch etherified with 2-hydroxypropyl, for example, as sold by National Starch under the trade name Amaze®.

But nonionic, fully synthetic polymers, such as polyvinyl alcohol or polyvinylpyrrolidinone, can be also used as thickening agents as contemplated herein. Preferred nonionic, fully synthetic polymers are, for example, sold by BASF under the trade name Luviskol®. Such nonionic polymers, in addition to their excellent thickening properties, also enable a significant improvement in the sensory feeling of the resulting preparations.

Phyllosilicates (polymeric, crystalline sodium disilicates) have proven to be particularly suitable as inorganic thickening agents in the context of the present disclosure. In particular clays, in particular magnesium aluminum silicates, such as bentonite, in particular smectites such as montmorillonite or hectorite, which may optionally be modified are also suitable, and synthetic layered silicates such as magnesium phyllosilicate sold by Süd Chemie under the trade name Optigel®, are preferred.

To further increase the performance of the oxidizing agent preparation, at least one optionally hydrated $SiO_2$ compound may additionally be added to the composition as contemplated herein. It may be preferred as contemplated herein, to use the optionally hydrated $SiO_2$ compounds in amounts of from about 0.05% by weight to about 15% by weight, particularly preferably in amounts of from about 0.15% by weight to about 10% by weight and very particularly preferably used in amounts of from about 0.2% by weight to about 5% by weight, each based on the anhydrous composition as contemplated herein. The quantity specifications in each case reflect the content of $SiO_2$ compounds (without their water content) in the agents.

The present disclosure is subject in principle to no restrictions with regard to the optionally hydrated $SiO_2$ compounds. Preference is given to silicic acids, their oligomers and polymers, and salts thereof. Preferred salts are the alkali metal salts, in particular potassium and sodium salts. The sodium salts are most preferred.

The optionally hydrated $SiO_2$ compounds can be present in various forms. According to the present disclosure, the $SiO_2$ compounds are preferably used in the form of silica gels or particularly preferably as water glass. These $SiO_2$ compounds may be partially present in aqueous solution.

Very particularly preferred as contemplated herein are water glasses which are formed from a silicate of the formula $(SiO_2)n(Na_2O)_m(K_2O)_p$, where n stands for a positive rational number and m and p independent of one other stand for a positive rational number or 0, with the provisos that at least one of the parameters m or p is different from 0 and the ratio between n and the sum of m and p is between from about 1:4 and about 4:1. Preference is given to metasilicates in which the ratio between n and the sum of m and p is about 1:2 or less.

In addition to the components described by the additivity formula, the water glasses may contain other additives in small amounts, such as phosphates or magnesium salts.

According to the present disclosure, particularly preferred water glasses are sold, among others, by Henkel under the names Ferrosil® 119, Natronwasserglas 40/42, Portil® A, Portil® AW and Portil® W and by Akzo under the name Britesil® C20.

Preferably, the preparation (A) and/or optionally the oxidizing agent preparation (B) are formulated as flowable preparations.

Preferably, an emulsifier or a surfactant is added to the flowable preparations (A) and/or (B), wherein surface-active substances are referred to as surfactants or as emulsifiers, depending on the field of application, and anionic, cationic, zwitterionic, amphoteric and nonionic surfactants and emulsifiers are selected. These substances are described in detail below.

All anionic surface-active substances suitable for use on the human body are suitable anionic surfactants in preparations as contemplated herein. These are characterized by a water-solubilizing, anionic group such as a carboxylate, sulfate, sulfonate or phosphate group and a lipophilic alkyl group having from about 8 to about 30 carbon atoms. In addition, glycol or polyglycol ether groups, ester, ether and amide groups and hydroxyl groups may be present in the molecule. Examples of suitable anionic surfactants are, in each case in the form of the sodium, potassium and ammonium and the mono-, di- and trialkanolammonium salts having from about 2 to about 4 C atoms in the alkanol group,

- linear and branched fatty acids having from about 8 to about 30 carbon atoms (soaps),
- ether carboxylic acids of the formula $RO(CH_2CH_2O)_xCH_2COOH$, in which R is a linear alkyl group having from about 8 to about 30 carbon atoms and x=0 or from about 1 to about 16,
- acylsarcosides having from about 8 to about 24 carbon atoms in the acyl group,
- acyltaurides having from about 8 to about 24 carbon atoms in the acyl group,
- acyl isethionates having from about 8 to about 24 carbon atoms in the acyl group,
- sulfosuccinic acid mono- and -dialkylesters having from about 8 to about 24 carbon atoms in the alkyl group and
- sulfosuccinic acid mono-alkyl polyoxyethyl esters having from about 8 to about 24 C atoms in the alkyl group and from about 1 to about 6 oxyethyl groups,
- linear alkanesulfonates having from about 8 to about 24 C atoms,
- linear a-olefin sulfonates having from about 8 to about 24 carbon atoms,
- sulfonates of unsaturated fatty acids having from about 8 to about 24 C atoms and from about 1 to about 6 double bonds, a-sulfofatty acid methyl esters of fatty acids having from about 8 to about 30 C atoms,
- alkyl sulfates and alkyl ether sulfates of the formula $RO(CH_2CH_2O)_xSO_3H$, in which R is a preferably linear alkyl group having from about 8 to about 30 C atoms and x=0 or from about 1 to about 12,
- mixtures of surface-active hydroxysulfonates,
- sulfated hydroxyalkylpolyethylene and/or hydroxyalkylene glycol ethers,
- esters of tartaric acid and citric acid with alcohols which are addition products of from about 2 to about 15 molecules of ethylene oxide and/or propylene oxide with fatty

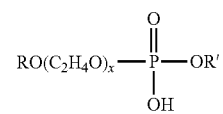

alcohols containing from about 8 to about 22 carbon atoms, alkyl and/or alkenyl ether phosphates of the formula in which R stands for an aliphatic, optionally unsaturated hydrocarbon radical having from about 8 to about 30 carbon atoms, R' stands for hydrogen, a radical (CH$_2$CH$_2$O)$_y$R and x and y independently of one another stand for a number from about 1 to about 10, sulfated fatty acid alkylene glycol esters of the formula RC(O)O(alkO)$_n$SO$_3$H, in which R stands for a linear or branched, aliphatic, saturated and/or unsaturated alkyl radical having from about 6 to about 22 C atoms, alk stands for CH$_2$CH$_2$, CHCH$_3$CH$_2$ and/or CH$_2$CHCH$_3$ and n stands for a number from about 0.5 to about 5, monoglyceride sulfates and monoglyceride ether sulfates.

Preferred anionic surfactants are alkyl sulfates, alkyl ether sulfates and ether carboxylic acids having from about 10 to about 18 carbon atoms in the alkyl group and up to about 12 glycol ether groups in the molecule.

Zwitterionic surfactants are those surface-active compounds which carry at least one quaternary ammonium group and at least one carboxylate, sulfonate or sulfate group in the molecule.

Particularly suitable zwitterionic surfactants are the so-called betaines such as the N-alkyl-N,N-dimethylammonium glycinates, for example, the coco-dimethylammonium-glycinate, N-acyl-aminopropyl-N,N-dimethylammonium glycinates, for example, the cocosacylaminopropyl-dimethylammoniumglycinate, and 2-alkyl-3-carboxymethyl-3-hydroxyethyl-imidazolines each having from about 8 to about 18 carbon atoms in the alkyl or acyl group, and the cocoacylamino-ethylhydroxyethyl-carboxymethylglycinates. An exemplary zwitterionic surfactant is the fatty acid amide derivative known by the INCI name Cocamidopropyl Betaine.

Amphoteric surfactants are understood to mean those surface-active compounds which, apart from a C$_8$-C$_2$4-alkyl or -acyl group in the molecule, contain at least one free amino group and at least one —COOH or —SO$_3$H group and which are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having from about 8 to about 24 C atoms in the alkyl group. Particularly preferred amphoteric surfactants are the N-cocoalkylaminopropionates, cocoacylaminoethylaminopropionate and C-I$_2$-Cl$_8$ acylsarcosine.

Furthermore, it has proved to be advantageous when the dyeing and lightening agents as contemplated herein contain further nonionic surface-active substances. Nonionic surfactants contain as a hydrophilic group, for example, a polyol group, a polyalkylene glycol ether group or a combination of polyol and polyglycol ether groups. Such compounds are, for example, addition products of from about 1 to about 50 moles of ethylene oxide and/or from about 0 to about 5 moles of propylene oxide to linear and branched fatty alcohols having from about 8 to about 30 carbon atoms, such as, for example, lauryl, myristyl, cetyl, but also stearyl, isostearyl and oleyl alcohol, to fatty acids having from about 8 to about 30 carbon atoms and to alkylphenols having from about 8 to about 15 carbon atoms in the alkyl group, having a methyl or C$_2$-C$_6$ alkyl radical end-capped addition products of from about 1 to about 50 moles of ethylene oxide and/or from about 0 to about 5 moles of propylene oxide to linear and branched fatty alcohols having from about 8 to about 30 carbon atoms, to fatty acids having from about 8 to about 30 carbon atoms and to alkylphenols having from about 8 to about 15 carbon atoms in the alkyl group, such as, for example, those types available under the trade names Dehydol® LS, Dehydol® LT (Cognis), polyglycerol esters and alkoxylated polyglycerol esters, such as poly(3)glycerol diisostearate (commercial product: Lameform® TGI (Henkel)) and poly(2)glycerinpolyhydroxy stearate (commercial product: Dehymuls® PGPH (Henkel)), polyol fatty acid esters, such as the commercial product Hydagen HSP (Cognis) or Sovermol types (Cognis), higher alkoxylated, preferably propoxylated and in particular ethoxylated, mono-, di- and triglycerides, such as glycerol monolaurate+20 ethylene oxide and glycerol monostearate+20 ethylene oxide, amine oxides, hydroxy mixed ethers, sorbitan fatty acid esters and addition products of ethylene oxide to sorbitan fatty acid esters such as the polysorbates and sorbitan monolaurate+20 moles of ethylene oxide (EO), sugar fatty acid esters and addition products of ethylene oxide to sugar fatty acid esters, addition products of ethylene oxide to fatty acid alkanolamides and fatty amines, fatty acid N-alkyl glucamides, alkylphenols and alkylphenol alkoxylates having from about 6 to about 21, in particular from about 6 to about 15 carbon atoms in the alkyl chain and from about 1 to about 30 ethylene oxide and/or propylene oxide units. Preferred representatives of this class are, for example, nonylphenol+9 EO and octylphenol+8 EO;

alkyl polyglycosides corresponding to the general formula RO-(Z)$_x$, where R stands for alkyl, Z stands for sugar and x stands for the number of sugar units. The alkylpolyglycosides which can be used as contemplated herein can only contain one particular alkyl radical R. Usually, however, these compounds are prepared starting from natural fats and oils or mineral oils. In this case, the alkyl radicals R are mixtures corresponding to the starting compounds or corresponding to the respective reworking of these compounds.

The alkoxylated homologs of said alkyl polyglycosides can also be used as contemplated herein. These homologs may contain on average up to about 10 ethylene oxide and/or propylene oxide units per alkyl glycoside unit.

The anionic, nonionic, zwitterionic or amphoteric surfactants are used in amounts of from about 0.1 to about 45% by weight, preferably from about 1 to about 30% by weight and very particularly preferably from about 1 to about 15% by weight, based on the total amount of the ready-to-use agent.

Also preferred as contemplated herein are cationic surfactants of the type of quaternary ammonium compounds, esterquats and amidoamines. Preferred quaternary ammonium compounds are ammonium halides, in particular, chlorides and bromides, such as alkyltrimethylammonium chlorides, dialkyldimethylammonium chlorides and trialkylmethylammonium chlorides, for example, cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the above-mentioned surfactants preferably have from about 10 to about 18 carbon atoms. Further cationic surfactants which can be used as contemplated herein are the quaternized protein hydrolysates.

The alkylamidoamines are usually prepared by amidation of natural or synthetic fatty acids and fatty acid cuts with dialkylaminoamines and are characterized, in addition to a good conditioning effect, in particular by their good biodegradability. A particularly suitable compound as contemplated herein from this group of substances is stearamidopropyl dimethylamine commercially available under the name Tegoamid® S 18.

Also very readily biodegradable are quaternary ester compounds, so-called "esterquats". Esterquats are known substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold under the trade names Stepantex®, Dehyquart® and Armocare®. The products Armocare® VGH-70, an N,N-bis(2-palmitoyloxyethyl) dimethylammonium chloride, and Dehyquart® F-75, Dehyquart® C-4046, Dehyquart® L80 and Dehyquart® AU-35 are examples of such esterquats.

The cationic surfactants are contained in the agents used as contemplated herein preferably in amounts of from about 0.05 to about 10% by weight, based on the total agent. Amounts of from about 0.1 to about 5% by weight are particularly preferred.

In an exemplary embodiment, nonionic, zwitterionic and/or amphoteric surfactants and mixtures thereof may be preferred.

In a further preferred embodiment, the effect of the active ingredient as contemplated herein can be increased by emulsifiers. Such emulsifiers are, for example,
- addition products of from about 4 to about 30 moles of ethylene oxide and/or from about 0 to about 5 moles of propylene oxide to linear fatty alcohols having from about 8 to about 22 carbon atoms, to fatty acids having from about 12 to about 22 carbon atoms and to alkylphenols having from about 8 to about 15 carbon atoms in the alkyl group,
- $C_{12}$-$C_{22}$ fatty acid mono- and diesters of addition products of from about 1 to about 30 moles of ethylene oxide to polyols having from about 3 to about 6 carbon atoms, in particular to glycerol,
- ethylene oxide and polyglycerol addition products to methyl glucoside fatty acid esters, fatty acid alkanolamides and fatty acid glucamides,
- $C_8$-$C_{22}$ alkylmono- and -oligoglycosides and their ethoxylated analogs, wherein oligomerization degrees of from about 1.1 to about 5, in particular from about 1.2 to about 2.0, and glucose as a sugar component are preferred, mixtures of alkyl-(oligo) glucosides and fatty alcohols, for example, the commercially available product Montanov® 68,
- addition products of from about 5 to about 60 moles of ethylene oxide to castor oil and hydrogenated castor oil, partial esters of polyols having from about 3 to about 6 carbon atoms with saturated fatty acids having from about 8 to about 22 carbon atoms,
- sterols, wherein sterols are understood to mean a group of steroids which carry a hydroxyl group on C-atom 3 of the steroid skeleton and are isolated both from animal tissue (zoosterols) and from vegetable fats (phytosterols). Examples of zoosterols are cholesterol and lanosterol. Examples of suitable phytosterols are ergosterol, stigmasterol and sitosterol. Mushrooms and yeasts are also used to isolate sterols, the so-called mycosterols. Phospholipids, primarily glucose phospholipids, which, for example, are obtained as lecithins or phosphatidylcholines from, for example, egg yolk or plant seeds (for example, soybeans),
- fatty acid esters of sugars and sugar alcohols, such as sorbitol
- polyglycerols and polyglycerol derivatives such as polyglycerol poly-12-hydroxystearate (commercial product Dehymuls® PGPH)
- linear and branched fatty acids having from about 8 to about 30 C atoms and their Na, K, ammonium, Ca, Mg and Zn salts.

The agents as contemplated herein may contain emulsifiers preferably in amounts of from about 0.1 to about 25% by weight, in particular from about 0.5 to about 15% by weight, based on the total amount of the ready-to-use agent.

Nonionic emulsifiers or surfactants having an HLB value of from about 10 to about 15 may be particularly preferred as contemplated herein. Among the emulsifier types mentioned, the emulsifiers which do not contain any ethylene oxide and/or propylene oxide in the molecule may be very particularly preferred.

Furthermore, the agents as contemplated herein may contain further active ingredients, auxiliaries and additives, such as, for example
- nonionic polymers such as vinylpyrrolidinone/vinyl acrylate copolymers, polyvinylpyrrolidinone, vinylpyrrolidinone/vinyl acetate copolymers, polyethylene glycols and polysiloxanes;
- silicones such as volatile or nonvolatile, straight-chain, branched or cyclic, crosslinked or uncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers with non-silicone-containing organic skeleton or with polysiloxane skeleton, such as, for example, the commercial product Abil B 8832 sold by Degussa under the INCI name Bis-PEG/PPG-20/20 Dimethicone, or mixtures thereof;
- cationic polymers such as quaternized cellulose ethers, polysiloxanes having quaternary groups, dimethyldiallylammonium chloride polymers, acrylamide-dimethyldiallyl-ammonium chloride copolymers, with diethyl sulfate quaternized dimethylaminoethylmethacrylate-vinylpyrrolidinone copolymers, vinylpyrrolidinone-imidazolinium methochloride copolymers, and quaternized polyvinyl alcohol;
- zwitterionic and amphoteric polymers such as acrylamidopropyltrimethylammonium chloride/acrylate copolymers and octylacrylamide/methylmethacrylate/tert-butylaminoethylmethacrylate/2-hydroxypropylmethacrylate copolymers, diallyldimethylammonium chloride/acrylate copolymers, t-butylaminoethylmethacrylate/N-(1,1,3,3-tetramethylbutyl)acrylic amide/acrylate(/methacrylate) copolymers,
- anionic polymers such as polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers, and acrylic acid/ethyl acrylate/N-t-butyl acrylamide terpolymers, structurants such as glucose, maleic acid and lactic acid, hair conditioning compounds such as phospholipids, such as soybean lecithin, egg lecithin and cephalins and silicone oils, perfume oils, dimethylisosorbide and cyclodextrins, solvents and mediators such as ethanol, isopropanol, ethylene glycol, propylene glycol, glycerol and diethylene glycol, active substances that improve fiber structure, in particular mono-, di- and oligosaccharides such as, for example, glucose, galactose, fructose, fructose and lactose, quaternized amines such as methyl-1-alkylamidoethyl-2-alkylimidazolinium methosulfate dyes for staining the agent, anti-dandruff agents such as Piroctone Olamine, Zinc Omadine and Climbazole, amino acids and oligopeptides, in particular arginine and/or serine, animal and/or plant-based protein hydrolysates, such as elastin, collagen, keratin, silk and milk protein protein hydrolysates, or almond, rice, pea, potato and wheat protein hydrolysates, and in the form of their fatty acid condensation products or optionally anionically or cationically modified derivatives, vegetable oils, for example, macadamia nut oil, kukui nut oil, palm oil, amaranth seed oil, peach kernel oil, avocado oil, olive oil, coconut oil, rapeseed oil, sesame oil, jojoba oil, soybean oil, peanut oil, evening primrose oil and tea tree oil, light stabilizers, in particular derivatized benzophenones, cinnamic acid derivatives and triazines, substances for adjusting the pH value, such as, for example, customary acids, in particular edible acids and bases, active ingredients such as panthenol, pantothenic acid, pantolactone, allantoin, pyrrolidinonecarboxylic acids and their salts, and bisabolol, polyphenols, in particular hydroxy cinnamic acids, 6,7-dihydroxycoumarins, hydroxybenzoic acids, catechins, tannins, leucoanthocyanidins, anthocyanidins, flavanones, flavones and flavonols; ceramides, preferably the sphingolipids such as ceramides I, ceramides II, ceramides 1, ceramides 2, ceramides 3, ceramides 5 and ceramides 6, or pseudoceramides, in particular N-($C_8$-$C_2$2-acyl)-($C_8$-$C_2$2-acyl) hydroxyproline, vitamins, provitamins and vitamin precursors, in particular those of groups A, $B_3$, $B_5$, $B_6$, C, E, F and H, plant extracts such as the extracts of aloe vera, angelica, anise, apricot, benzoin, bergamot, birch, stinging nettle, calmus, cassis, costus, mallow, oak bark, elemi, tarragon, spruce needle, galbanum, geranium, ginseng, grapefruit, guaiac wood, green tea, witch hazel, restharrow, hops, coltsfoot, ginger root, iris, jasmine, chamomile, cardamom, clover, burdock, pine, kiwi, coconut, cilantro, caraway, mountain pine, lavender, lemon grass, lily, lime, linden, litchi, macis, mallow, almond, mango, melissa, melon, meristem, myrrh, neroli, olibanum, opoponax, orange, patchouli, petitgrain, pine, quendel, rooibos, roses, rosemary, horse chestnut, sandalwood, sage, horsetail, yarrow, celery, fir, thyme, juniper, grape leaves, hawthorn, wheat, meadowfoam, ylang-ylang, cedar and lemon.

Cholesterol, consistency enhancers such as sugar esters, polyol esters or polyol alkyl ethers, fats and waxes such as spermaceti, beeswax, montan wax and paraffins, fatty acid alkanolamides, swelling and penetration substances such as glycerol, propylene glycol monoethyl ether, carbonates, hydrocarbonates, guanidines, ureas and primary, secondary and tertiary phosphates, opacifiers such as latex, styrene/PVP and styrene/acrylamide copolymers pearlescing agents such as ethylene glycol mono- and distearate and PEG-3-distearate, pigments, stabilizing agents for hydrogen peroxide and other oxidizing agents, propellants such as propane-butane mixtures, $N_2O$, dimethyl ether, $CO_2$ and air, antioxidants.

The selection of these further substances will be made by those skilled in the art according to the desired properties of the agents.

With regard to further optional components and the amounts of these components used, reference is expressly made to the relevant manuals known to the person skilled in the art, e.g., Kh. Schrader, Grundlagen and Rezepturen der Kosmetika, 2nd edition, Hüthig book publishing house, Heidelberg, 1989.

The additional active ingredients and auxiliaries are preferably used in the agents as contemplated herein in amounts of from about 0.0001 to about 10% by weight, in particular from about 0.0005 to about 5% by weight, based on the total weight of the application mixture.

For the strong lightening of very dark hair, the sole use of hydrogen peroxide or its addition products to organic or inorganic compounds is often insufficient. The agents as contemplated herein may therefore additionally contain further blonding and/or bleaching agents.

If a strong lightening is desired in addition to the coloring of the keratinic fiber, it is therefore preferred as contemplated herein when additionally, a bleaching preparation (C) containing at least one bleach activator, the mixture of oxidizing agent preparation (B) and the preparation (A) containing at least one oxidation dye precursor according to formula (I) is admixed.

It may be irrelevant whether first a mixture of (A) and (B) is prepared, and then the bleaching preparation (C) is added, or whether a different order of mixing of the individual components is used. It is preferred to mix the individual preparations in the earliest possible chronological order and preferably to apply the ready-to-use agent promptly to the keratinic fibers.

A further embodiment of the present application is therefore an agent for bleaching and dyeing keratinic fibers, characterized in that it is prepared before use by mixing at least one oxidizing agent preparation (B) containing at least one oxidizing agent selected from hydrogen peroxide and its addition compounds to solid carriers, at least one bleaching preparation (C) containing at least one bleaching power enhancer, and at least one preparation (A) containing, in a cosmetic carrier, at least one oxidation dye precursor according to formula (I).

In a further embodiment, it is preferred when the colorant as contemplated herein additionally contains at least one inorganic peroxo compound as a bleaching preparation (C). Preferably, the inorganic peroxo compound is selected from ammonium persulfate, alkali metal persulfates, ammonium peroxomonosulfate, alkali metal hydrogen peroxomonosulfates, alkali metal peroxodiphosphates and alkaline earth metal peroxides. Particularly preferred inorganic peroxy compounds as bleaching power enhancers are ammonium peroxodisulfate, potassium peroxodisulfate, sodium peroxodisulfate, potassium hydrogen peroxomonosulfate, potassium peroxodiphosphate, magnesium peroxide and barium peroxide, in particular ammonium peroxodisulfate, potassium peroxodisulfate and sodium peroxodisulfate.

The inorganic peroxo compounds are preferably contained in an amount of from about 0.1 to about 25% by weight, in particular in an amount of from about 0.5 to about 15% by weight, based on the total weight of the ready-to-use agent.

The use of persulfate salts or peroxodisulfate salts is generally carried out in the form of an optionally dust-free powder or a molding pressed into the mold.

However, it may be advantageous as contemplated herein when the agents are free of inorganic peroxo compounds. However, the agents as contemplated herein may therefore, instead of and/or in addition to the solid peroxo compounds, contain a further bleaching power enhancer.

Additional bleaching power enhancers which can be used in the context of this present disclosure are compounds which, under perhydrolysis conditions, give aliphatic peroxycarboxylic acids, such as acylated alkylenediamines, in particular tetraacetylethylenediamine (TAED), and/or substituted perbenzoic acid, carbonic acid derivatives, in particular ammonium bicarbonate, ammonium carbonate, sodium bicarbonate, sodium carbonate, potassium bicarbonate, potassium carbonate and calcium carbonate, alkyl carbonates and carbamates, and silyl carbonates and carbamates.

The bleaching power enhancers used in addition to or instead of peroxo compounds are preferably contained in amounts of from about 0.05 to about 10% by weight, in particular in amounts of from about 0.2 to about 5% by weight, in each case based on the total weight of the ready-to-use cosmetic agent.

Although in principle there are no restrictions with respect to the formulation of the bleaching preparation (C), it has proved to be preferred as contemplated herein when the preparation (C) is formulated anhydrous.

Anhydrous in the context of the present disclosure means a water content based on the preparation (C) of less than about 5% by weight, in particular less than about 2% by weight. Bleaching preparations which contain less than about 0.1% by weight of water may be very particularly preferred as contemplated herein. The preparation (C) is preferably formulated as a powder or as an anhydrous paste.

In a further preferred embodiment, the agent in the preparation (C) may contain at least one cationic pyridinium derivative as a bleaching power enhancer. In particular, agents as contemplated herein are preferred which contain as a cationic pyridinium derivative at least one compound from 2-acetyl-1-methylpyridinium-p-toluenesulfonate and/or 4-acetyl-1-methylpyridinium-p-toluenesulfonate and/or N-methyl-3,4-dihydroisoquinolinium p-toluenesulfonate.

An inventively preferred embodiment of the present disclosure is that the ready-to-use agent has a pH between from about 7 and about 11, in particular between from about 8 and about 10.5, particularly preferably between from about 8.5 and about 10.0.

Usually, the pH value is adjusted with pH adjusters. Common acidification and alkalizing agents which are familiar to the person skilled in the art are used to adjust the pH value. The alkalizing agents which can be used for adjusting the pH are typically selected from inorganic salts, in particular the alkali metals and alkaline earth metals, organic alkalizing agents, in particular amines, basic amino acids and alkanolamines, and ammonia. Acidification agents which are preferred as contemplated herein are edible acids, such as citric acid, acetic acid, malic acid or tartaric acid, and dilute mineral acids.

For the purposes of the present disclosure, the pH values are pH values measured at a temperature of about 22° C.

Organic alkalizing agents which can be used as contemplated herein are preferably selected from alkanolamines of primary, secondary or tertiary amines having a $C_2$-$C_6$ alkylbasic body which carries at least one hydroxyl group. Particularly preferred alkanolamines are selected from the group 2-aminoethane-1-ol (monoethanolamine), 2-amino-2-methylpropan-1-ol, 2-amino-2-methyl-propane-1,3-diol and triethanolamine.

However, it has been found in the context of the examinations regarding the present disclosure that further preferred agents as contemplated herein are characterized in that they additionally contain an inorganic alkalizing agent. The inorganic alkalizing agent according to the present disclosure is preferably selected from the group formed from sodium hydroxide, potassium hydroxide, calcium hydroxide, barium hydroxide, sodium phosphate, potassium phosphate, sodium silicate, potassium silicate, sodium carbonate and potassium carbonate. Very particular preference is given to sodium hydroxide and/or potassium hydroxide.

The basic amino acids which can be used as alkalizing agents as contemplated herein are preferably selected from the group formed from L-arginine, D-arginine, D/L-arginine, L-lysine, D-lysine, D/L-lysine, particularly preferably L-arginine, D-arginine, D/L-arginine are used as an alkalizing agent as contemplated herein.

Finally, a further preferred alkalizing agent is ammonia.

The alkalizing agents are preferably contained in an amount of from about 0.05 to about 10% by weight, in particular from about 0.5 to about 5% by weight, in each case based on the total weight of the ready-to-use agent.

As already mentioned, the agents as contemplated herein can also be prepared directly before use from two or more separately packaged preparations. This is particularly useful for separating incompatible ingredients to avoid premature reaction. Separation into multicomponent systems is particularly suitable where incompatibilities of the ingredients are to be expected or feared. The ready-to-use agent in such systems is prepared by the consumer just prior to use by mixing the components. A dyeing and/or lightening agent in which the oxidation dye precursors are initially present separate from the oxidizing agent preparation, preferably containing hydrogen peroxide, is preferred.

An exemplary presentation form of the agent as contemplated herein is a packaging unit (kit-of-parts), which contains in separately packaged containers in a container A contains at least one preparation (A), containing in a cosmetic carrier at least one oxidation dye precursor according to the formula (I), and in a container B, at least one oxidizing agent preparation (B) containing at least one oxidizing agent in a cosmetic carrier, If a particularly strong lightening effect is desired, an exemplary further presentation form of the agent as contemplated herein is a packaging unit (kit-of-parts), which contains in separately packaged containers in a container A at least one preparation (A), containing in a cosmetic carrier at least one oxidation dye precursor according to the formula (I), in a container B, at least one oxidizing agent preparation (B) containing at least one oxidizing agent, and in a container C, at least one bleaching preparation (C) containing at least one bleaching power enhancer.

The multi-component packaging unit (kit-of-parts) preferably additionally contains an instruction manual. In addition, it may be preferred when an application aid, such as a comb or a brush, and/or personal protective equipment, such as disposable gloves, are also included in the kit.

With regard to further preferred embodiments of the multi-component packaging unit (kit-of-parts), what has been said about the agents as contemplated herein applies mutatis mutandis.

The actual hair colorant is expediently prepared immediately before use by mixing the preparations (A) with (B) and optionally (C). The application temperatures can range between from about 15 and about 40° C. After a contact time of from about 5 to about 45 minutes, the hair colorant is removed by rinsing of the hair to be dyed. The washing with a shampoo is omitted when a strong surfactant-containing carrier, such as a dyeing shampoo, has been used.

During the contact time of the agent on the fiber, it may be advantageous to assist the dyeing process by supplying heat. The heat supply can be done by an external heat source, such as warm air of a hot air blower, and, in particular in a hair dye on living subjects, by the body temperature of the subject. In the latter possibility, usually the party to be dyed is covered with a hood. In particular, the temperature during the exposure time is between from about 10° C. and about 45° C., in particular between from about 20° C. and about 40° C. The colorants as contemplated herein give intensive colorings even at physiologically compatible temperatures of below about 45° C. They are therefore particularly suitable for dyeing human hair.

Another object of the present disclosure is the use of an agent as contemplated herein in human hair colorants to improve the gray coverage, the leveling, the color intensity, the durability and/or the coloration of the dyeing results.

With regard to further preferred embodiments of the methods and uses as contemplated herein, the statements made with regard to the agents as contemplated herein apply mutatis mutandis.

Finally, a further subject of the present disclosure relates to compounds according to formula (I) of the first subject of the present disclosure. With respect to further preferred embodiments of these compounds, what has been said about the agent as contemplated herein applies mutatis mutandis.

EXAMPLES

Synthesis Examples a) Basic Structure
i) Synthesis of 6-nitro-3H-1,3-benzoxazol-2-one

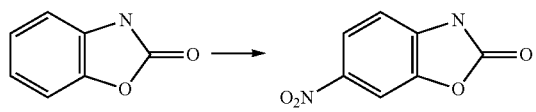 [SMILES: O=c1[nH]c2ccccc2o1 ; O=c1[nH]c2ccc([N+](=O)[O-])cc2o1]

40.0 g (0.30 mol) of 2-benzoxazolinone were dissolved with stirring at room temperature in 600.0 ml (0.30 mole) of 68% nitric acid. It was then heated to 50° C. and stirred at this temperature for three hours. The reaction was stirred for a further 16 h at room temperature. After completion of the reaction, the mixture was poured into about 2.0 l of ice water, precipitated substance was filtered off, washed neutral and dried. After drying, 6-nitro-3H-1,3-benzoxazol-2-one (39.1 g, 72%) was obtained as a pale yellow solid.

$^1$H-NMR (300 MHz, d$_6$-DMSO): δ=7.25 (d, 1 H, 4-H), 8.10 (d, 1 H, 5-H), 8.17 (s, 1 H, 7-H), 12.43 (br s, 1 H, NH).

ii) Synthesis of 4,6-dinitro-3H-1,3-benzoxazol-2-one

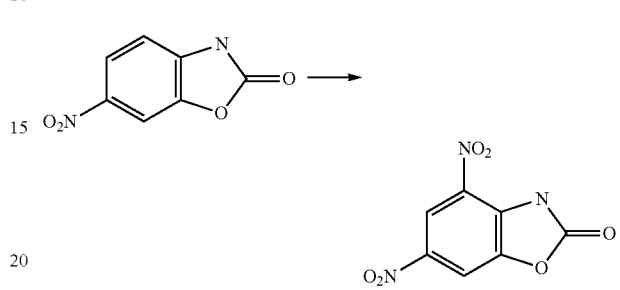

25.0 ml of concentrated sulfuric acid were added dropwise in 160.0 ml of nitric acid (fuming) at 0° to 5° C. while maintaining temperature and stirred for ten minutes. Subsequently, 6-nitro-3H-1,3-benzoxazol-2-one (39.0 g, 0.22 mol) was added portionwise at this temperature and stirred for 15 min. After completion of the reaction, the mixture was poured into about 1.5 liters of ice water and extracted with ethyl acetate. The organic phase was washed with NaHCO$_3$— and saturated NaCl solution until the washings were neutral, dried via sodium sulfate and carefully concentrated. The residue was recrystallized from 40 ml of water and 90 ml of 1,4-dioxane to remove the regioisomer.

After drying, 4.6-dinitro-3H-1,3-benzoxazol-2-one (21.5 g, 43%) was obtained as a pale yellow solid.

$^1$H-NMR (300 MHz, d$_6$-DMSO): δ=8.62 (d, 1 H, 5-H), 8.70 (s, 1 H, 7-H), 12.90 (br s, 1 H, NH).

$^{13}$C-NMR (125 MHz, d$_6$-DMSO): δ=110.2 (7-C), 115.5 (5-C), 130.1 (9-C), 133.7 (4-C), 141.1 (6-C), 145.3 (8-C), 154.3 (2-C).

iii) Synthesis of 2-amino-3,5-dinitro-phenol

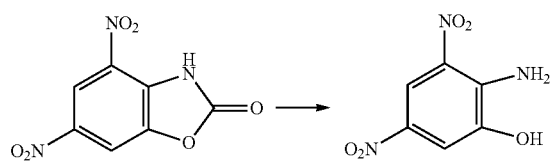

A solution of 10.5 g (46.6 mmol) of 4,6-dinitro-3H-1,3-benzoxazol-2-one in 250 ml of sodium hydroxide solution (1%) was stirred at 50° C. for 22 h. It was then neutralized with half-concentrated hydrochloric acid with cooling and extracted with ethyl acetate. The organic phase was washed with saturated NaCl solution, dried via sodium sulfate and concentrated.

After drying, 2-amino-3,5-dinitrophenol (6.4 g, 70%) was obtained as a dark brown solid.

$^1$H-NMR (300 MHz, d$_6$-DMSO): δ=7.56 (s, 1 H, 6-H), 7.78 (br s, 1 H, NH). 8.41 (s, 1 H, 4-H), 11.48 (s, 1 H, OH).

b) Target molecule: 6-(2-ethoxyethoxy) benzene-1,2,4-triamine (hydrochloride) E1 i) Synthesis of 2-(2-ethoxyethoxy)-4,6-dinitroaniline

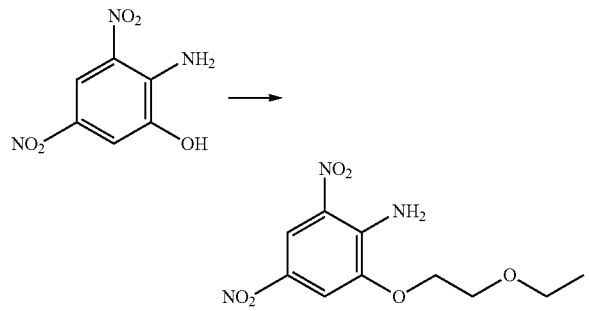

A solution of 4.4 g (22.1 mmol) of 2-amino-3,5-dinitrophenol in 10 ml of dimethylformamide was added to a suspension of 3.7 g (26.5 mmol) of potassium carbonate in 50 ml of dimethylformamide and stirred at 80° C. for 30 min. Subsequently, a solution of 3.4 g (22.1 mmol) of (2-bromoethyl) ethyl ether in 10 ml of dimethylformamide was added dropwise and stirred at 80° C. for 1 h. After cooling to room temperature, the solid was filtered off and the filtrate was concentrated.

After drying, 2-(2-ethoxyethoxy)-4,6-dinitroaniline (6.0 g, 78%) was obtained as a dark brown solid.

$^1$H-NMR (300 MHz, d$_6$-DMSO): δ=1.12 (t, 3 H, 4'-CH$_3$), 3.51 (q, 2 H, 3'-CH$_2$), 3.81 (dd, 2 H, 2'-H$_2$), 4.34 (dd, 2 H, 1'-H$_2$), 7.79 (s, 1 H, 6-H), 8.52 (s, 1 H, 4-H).

$^{13}$C-NMR (125 MHz, d$_6$-DMSO): δ=15.4 (4'-C), 66.0 (3'-C), 68.3 (2'-C), 70.1 (1'-C), 109.4 (5-C), 115.6 (3-C), 128.5 (2-C), 134.6 (2-C), 142.6 (4-C), 147.7 (6-C).

ii) Synthesis of 6-(2-ethoxyethoxy) benzene-1,2,4-triamine (hydrochloride) E1

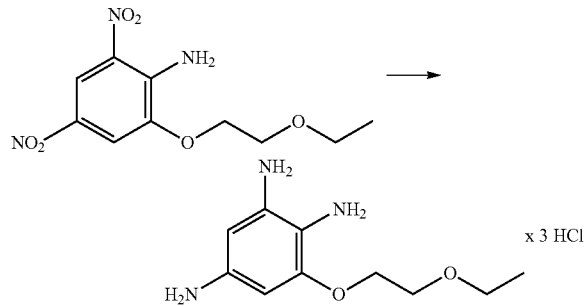

0.1 g of palladium on active charcoal (5%) in a low pressure hydrogenation apparatus as a catalyst was added to a solution of 6.0 g (22.1 mmol) of 2-(2-ethoxyethoxy)-4,6-dinitroaniline in 400 ml of ethanol and this was flooded with 1 bar of hydrogen gas at room temperature. It was shaken for 30 h under constant hydrogen pressure. Subsequently, the reaction mixture was poured into 250 ml of half-concentrated hydrochloric acid, the solid was filtered off and the filtrate was concentrated.

After drying, 6-(2-ethoxyethoxy) benzene-1,2,4-triamine (hydrochloride) (5.3 g, 75%) was obtained as a tan solid.

$^1$H-NMR (300 MHz, D$_2$O): δ=1.25 (t, 3 H, 4'-CH$_3$), 3.70 (q, 2 H, 3'-CH$_2$), 3.97 (dd, 2 H, 2'-H$_2$), 4.33 (dd, 2 H, 1'-H$_2$), 6.70 (s, 1 H, 6-H), 7.18 (s, 1 H, 4-H).

$^{13}$C-NMR (125 MHz, D$_2$O): δ=17.1 (4'-C), 69.7 (3'-C), 71.1 (2'-C), 71.4 (1'-C), 102.8 (5-C), 109.3 (3-C), 114.8 (2-C), 131.7 (2-C), 139.1 (4-C), 155.0 (6-C).

c) Target molecule: 6-(methoxyethoxy) benzene-1,2,4-triamine (hydrochloride) E2 i) Synthesis of 2-(2-ethoxyethoxy)-4,6-dinitroaniline

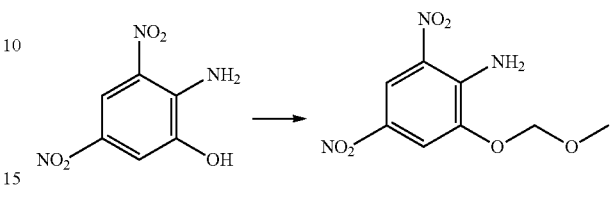

A solution of 4.4 g (22.1 mmol) of 2-amino-3,5-dinitrophenol in 10 ml of dimethylformamide was added to a suspension of 3.7 g (26.5 mmol) of potassium carbonate in 50 ml of dimethylformamide and stirred at 80° C. for 30 min. Subsequently, a solution of 2.1 g (22.1 mmol) of 2-methoxymethylchloride in 10 ml of dimethylformamide was added dropwise and stirred at 80° C. for 1 h. After cooling to room temperature, the solid was filtered off and the filtrate was concentrated.

After drying, 2-(methoxymethoxy) -4,6-dinitroaniline (5.2 g, 96%) was obtained as a black solid.

$^1$H-NMR (300 MHz, d$_6$-DMSO): δ=2.73 (s, 3 H, OMe), 2.98 (s, 2 H, 1'-H$_2$), 7.69 (s, 1 H, 6-H), 8.94 (s, 1 H, 4-H).

$^{13}$C-NMR (125 MHz, d$_6$-DMSO): δ=37.1 (OMe), 70.2 (1'-C), 100.6 (5-C), 101.3 (3-C), 126.8 (1-C), 138.5 (2-C), 147.6 (6-C), 162.7 (4-C).

ii) Synthesis of 6-(methoxymethoxy)benzene-1,2,4-triamine (hydrochloride) E2

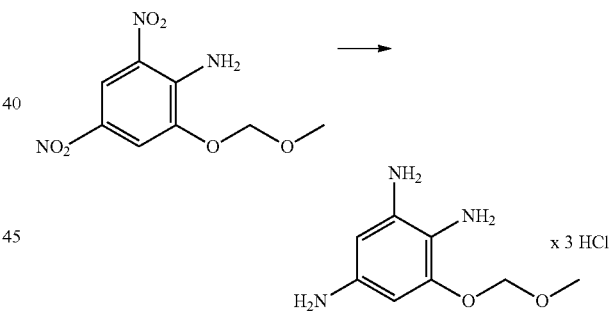

0.1 g of palladium on active charcoal (5%) in a low pressure hydrogenation apparatus as a catalyst was added to a solution of 5.2 g (21.1 mmol) of 2-(2-methoxyethoxy)-4,6-dinitroaniline in 400 ml of ethanol and this was flooded with 1 bar of hydrogen gas at room temperature. It was shaken for 30 h under constant hydrogen pressure. Subsequently, the reaction mixture was poured into 250 ml of half-concentrated hydrochloric acid, the solid was filtered off and the filtrate was concentrated.

After drying, 6-(methoxymethoxy) benzene-1,2,4-triamine (hydrochloride) (4.9 g, 80%) was obtained as a brown solid.

$^1$H-NMR (300 MHz, D$_2$O): δ=2.85 (s, 3 H, OMe), 3.48 (s, 2 H, 1'-H$_2$), 6.61 (s, 1 H, 6-H), 7.03 (s, 1 H, 4-H).

$^{13}$C-NMR (125 MHz, D$_2$O): δ=37.6 (OMe), 71.3 (1'-C), 106.6 (5-C), 108.9 (3-C), 132.0 (1-C), 141.3 (2-C), 153.8 (6-C), 159.6 (4-C).

d) Target molecule: 6-(methoxyethoxy) benzene-1,2,4-triamine (hydrochloride) E3 i) Synthesis of 2-(2-methoxyethoxy)-4,6-dinitroaniline

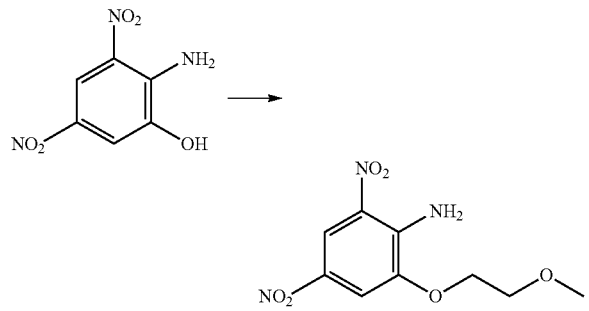

A solution of 3.4 g (17.1 mmol) of 2-amino-3,5-dinitrophenol in 10 ml of dimethylformamide was added to a suspension of 4.2 g (20.5 mmol) of potassium carbonate in 50 ml of dimethylformamide and stirred at 80° C. for 30 min. Subsequently, a solution of 2.1 g (22.1 mmol) of 1-bromo-2-methoxyethane in 10 ml of dimethylformamide was added dropwise and stirred at 80° C. for 1 h. After cooling to room temperature, the solid was filtered off and the filtrate was concentrated.

After drying, 2-(methoxymethoxy)-4,6-dinitroaniline (3.9 g, 89%) was obtained as a black solid.

$^1$H-NMR (300 MHz, $d_6$-DMSO): δ=3.35 (s, 3 H, OMe), 3.78 (dd, 2 H, 2'-$H_2$), 4.33 (dd, 2 H, 1'-$H_2$), 7.74 (s, 1 H, 6-H), 8.50 (s, 1 H, 4-H).

ii) Synthesis of 6-(methoxyethoxy) benzene-1,2,4-triamine

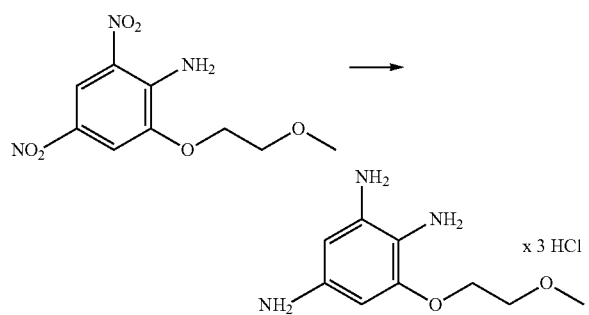

0.1 g of palladium on active charcoal (5%) in a low pressure hydrogenation apparatus as a catalyst was added to a solution of 3.9 g (15.2 mmol) of 2-(2-methoxyethoxy)-4,6-dinitroaniline in 400 ml of ethanol and this was flooded with 1 bar of hydrogen gas at room temperature. It was shaken for 30 h under constant hydrogen pressure. Subsequently, the reaction mixture was poured into 250 ml of half-concentrated hydrochloric acid, the solid was filtered off and the filtrate was concentrated.

After drying, 6-(methoxyethoxy) benzene-1,2,4-triamine (hydrochloride) (4.0 g, 86%) was obtained as a brown solid.

$^1$H-NMR (300 MHz, $d_6$-DMSO): δ=3.30 (s, 3 H, OMe), 3.71 (dd, 2 H, 1'-$H_2$), 4.03 (dd, 2 H, 1'-$H_2$), 6.00 (s, 1 H, 6-H), 6.58 (s, 1 H, 4-H).

$^{13}$C-NMR (125 MHz, $d_6$-DMSO): δ=59.6 (3'-C), 69.0 (2'-C), 69.6 (1'-C), 89.7 (5-C), 103.1 (3-C), 150.2 (2-C), 155.7 (2-C), 165.8 (4-C), 176.8 (6-C).

Dyeing Example 2.1. Preparation of the Coloring Creams

The following coloring creams were prepared:

| | |
|---|---|
| Hydrenol ® D[1] | 8.5% by weight |
| Lorol ® tech.[2] | 2.0% by weight |
| Texapon ® NSO[3] | 20.0% by weight |
| Dehyton ® K[4] | 12.5% by weight |
| Eumulgin ® B2[5] | 0.75% by weight |
| Sodium sulfite | 1.0% by weight |
| Ammonium sulfate | 1.0% by weight |
| Developer component | 3 mmol |
| Coupler component | 3 mmol |
| Water | ad 100 |

[1]$C_{16-18}$ fatty alcohol (INCI name: Cetearyl alcohol; Cognis)
[2]$C_{12-18}$ fatty alcohol (INCI name: Coconut alcohol; Cognis)
[3]Sodium lauryl ether sulfate (INCI name: Sodium Laureth Sulfate; 27.5%; Cognis)
[4]N,N-dimethyl-N-($C_{8-18}$-cocoamidopropyl) ammonium acetobetaine (about 30% active ingredient; INCI name: Aqua (Water), Cocamidopropyl Betaine) (Cognis)
[5]Cetylstearyl alcohol (20 EO) (INCI name: Ceteareth-20) (Cognis)

Hydrenol® D and Lorol® techn. were melted together with Texapon® NSO, Dehyton® K and Eumulgin® B2 at 80° C. Then, the melt was emulsified with the sodium sulfite and ammonium sulfate dissolved in a part of the water. The developer as contemplated herein was dissolved in a further portion of the specified amount of water with heating and added with stirring. The coupler was also dissolved in a portion of the specified amount of water and added with stirring. Then the formulation was filled up to 100% with water and stirred cold.

The dyeing cream obtained in this way was mixed in the ratio 1:1 with the following developer dispersion having a hydrogen peroxide content of 6%.

| | |
|---|---|
| Dipicolinic acid | 0.1% by weight |
| Sodium pyrophosphate | 0.03% by weight |
| Turpinal ® SL[6] | 1.50% by weight |
| Texapon ® N28[7] | 2.00% by weight |
| Acrysol ® 22[8] | 0.60% by weight |
| Hydrogen peroxide, 50% | 6.00% by weight |
| Sodium hydroxide, 45% | 0.80% by weight |
| Water | ad 100% by weight |

[6]1-hydroxyethane-1,1-diphosphonic acid (about 58-61% active ingredient content; INCI name: Etidronic Acid, Aqua (Water)) (Solutia)
[7]Sodium lauryl ether sulfate (INCI name: Sodium Laureth Sulfate; 26.5; Cognis)
[8]acrylic polymer (about 29.5-30.5% solids in water, INCI name: Acrylates/Steareth-20 Methacrylate Copolyme)

For the staining process, 4 times the amount of the ready-to-use mixture was applied to a strand of light blond hair (Kerling 10-0). After a contact time of 30 minutes at 32° C., the strands were rinsed and washed with a conventional shampoo. The coloring of the strands was visually assessed under the daylight lamp after drying. The dyeing results are summarized in the following tables.

| E1: Coloration with 6-(2-ethoxyethoxy)benzene-1,2,4-triamine (hydrochloride) E1 | | | |
|---|---|---|---|
| Example | Coupler component | Nuance obtained | Color intensity |
| 1 | Resorcinol | rose ash blond | +++ |
| 2 | 3-amino-2-methylamino-6-methoxypyridine | chestnut | +++ |
| 3 | 2-methylresorcinol | ash blond | ++ |

+++ high intensity
++ medium intensity
+ low intensity

E2: Coloration with 6-(2-methoxyethoxy)benzene-1,2,4-triamine (hydrochloride) E2

| Example | Coupler component | Nuance obtained | Color intensity |
|---|---|---|---|
| 1 | Resorcinol | sand blond | ++ |
| 2 | 3-amino-2-methylamino-6-methoxypyridine | brown-red | +++ |
| 3 | 2-methylresorcinol | sand blond | ++ |

+++ high intensity
++ medium intensity
+ low intensity

E3: Coloration with 6-(2-methoxyethoxy)benzene-1,2,4-triamine (hydrochloride) E3

| Example | Coupler component | Nuance obtained | Color intensity |
|---|---|---|---|
| 1 | Resorcinol | dark blond | +++ |
| 2 | 3-amino-2-methylamino-6-methoxypyridine | chestnut | +++ |
| 3 | 2-methylresorcinol | dark blond | +++ |

+++ high intensity
++ medium intensity
+ low intensity

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinic fibers, the agent comprising, in a cosmetic carrier, at least one compound of the formula (I) and/or a physiologically compatible salt of a compound of the formula (I),

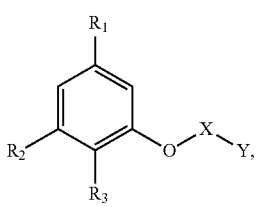

(I)

in which $R_1$, $R_2$, and $R_3$ each stand for an amino group, wherein the amino group may be substituted by a group Q,
Q stands for an alkyl group or an aryl group,
X stands for a $C_1$-$C_6$ alkyl group or a group of the general formula (II),

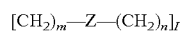

(II)

Z stands for an oxygen atom or an amino group,
m stands for a number from 1 to 2,
n stands for a number from 0 to 1,
l stands for a number from 1 to 3, and
Y stands for a hydrogen atom, a hydroxy group, an alkoxy group or an amino group, wherein the amino group may be substituted with one or two Q groups and Y stands for a hydrogen atom when n=0.

2. The agent according to claim 1, wherein the radicals $R_1$, $R_2$ and $R_3$ each stand for an $NH_2$ group, wherein Y stands for an $NH_2$ group, and/or wherein Z stands for an oxygen atom.

3. The agent according to claim 1, wherein the agent comprises at least one compound of the formula (I), which is selected from the group consisting of (2,3,5-triaminophenoxy) methanol, 6-(methoxymethoxy) benzene-1,2,4-triamine, (2,3,5-triaminophenoxy) methoxymethanol, 6-(methoxymethoxymethoxy) benzene-1,2,4-triamine, 2-(2,3,5-triaminophenoxy) ethanol, 6-(2-methoxyethoxy) benzene-1,2,4-triamine, 6-(methylaminoethoxy) benzene-1,2,4-triamine, 6-[(dimethylamino)methoxy] benzene-1,2,4-triamine, 6-(2-aminoethoxy) benzene-1,2,4-triamine, 6-[2-(methylamino)ethoxy] benzene-1,2,4-triamine, 6-[2-(dimethylamino)ethoxy] benzene-1,2,4-triamine, [(2,3,5-triaminophenoxy)methylamino] methanol, 6-[(methoxymethylamino)methoxy] benzene-1,2,4-triamine, 2-[2-(2,3,5-triaminophenoxy)ethylamino] ethanol, 6-[2(2-methoxyethylamino)ethoxy] benzene-1,2,4-triamine, the mixtures and/or physiologically compatible salts thereof.

4. The agent according to claim 1, wherein the agent comprises the compound(s) of the formula (I), their mixtures and/or their physiologically compatible salts in a proportion by weight of from about 0.001 to about 5.0% by weight.

5. The agent according to claim 1, wherein the agent comprises from about 0.001 to about 5.0% by weight of at least one coupler component, based on the total weight of the ready-to-use agent.

6. The agent according to claim 1, wherein the agent comprises 6-(methoxymethoxy) benzene-1,2,4-triamine and/or 6-(2-methoxyethoxy) benzene-1,2,4-triamine and/or a physiologically compatible salt thereof and one or more compounds selected from 5-amino-2-methylphenol, 1,3-bis (2,4-diaminophenoxy) propane, resorcinol, 2-methylresorcinol, 2-amino-3-hydroxypyridine, 3-amino-2-methylamino-6-methoxypyridine, 2,7-dihydroxynaphthalene and the physiologically compatible salts thereof.

7. An agent for dyeing keratinic fibers, the agent comprising, in a cosmetic carrier, at least one compound of the formula (I) and/or a physiologically compatible salt of a compound of the formula (I),

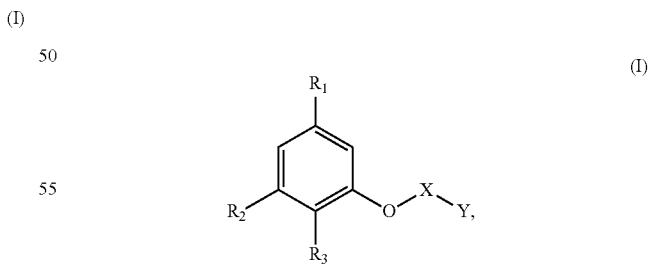

(I)

in which $R_1$, $R_2$, and $R_3$ each stand for an amino group, wherein the amino group may be substituted by a group Q,
Q stands for an alkyl group or an aryl group,
X stands for a $C_1$-$C_6$ alkyl group or a group of the general formula (II),

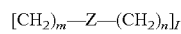

(II)

Z stands for an amino group, m stands for a number from 1 to 3, n stands for a number from 0 to 3, I stands for a number from 1 to 3, and Y stands for a hydrogen atom, a hydroxy group, an alkoxy group or an amino group, wherein the amino group may be substituted with one or two Q groups and Y stands for a hydrogen atom when n=0.

8. The agent according to claim 7, wherein the agent comprises at least one compound of the formula (I), which is selected from the group consisting of 6-(methylaminomethoxy) benzene-1,2,4-triamine, 6-[(dimethylamino)methoxy] benzene-1,2,4-triamine, 6-(2-aminoethoxy) benzene-1,2,4-triamine, 6-[2-(methylamino)ethoxy] benzene-1,2,4-triamine, 6-[2-(dimethylamino)ethoxy] benzene-1,2,4-triamine, [(2,3,5-triaminophenoxy)methylamino] methanol, 6-[(methoxymethylamino)methoxy] benzene-1,2,4-triamine, 2-[2-(2,3,5-triaminophenoxy)ethylamino] ethanol, 6-[2-(2-methoxyethylamino)ethoxy] benzene-1,2,4-triamine, the mixtures and/or physiologically compatible salts thereof.

9. An agent for dyeing keratinic fibers, the agent comprising, in a cosmetic carrier, at least one compound of the formula (I) and/or a physiologically compatible salt of a compound of the formula (I),

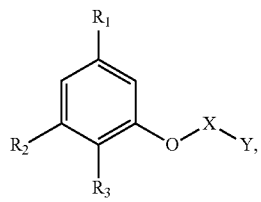

in which $R_1$, $R_2$, and $R_3$ each stand for an amino group, wherein the amino group may be substituted by a group Q, Q stands for an alkyl group or an aryl group, X stands for a $C_1$-$C_6$ alkyl group or a group of the general formula (II), $$[CH_2)_m—Z—(CH_2)_n]_I \qquad (II)$$

Z stands for an oxygen atom or an amino group, m stands for a number from 1 to 3, n stands for a number from 0 to 3, I stands for a number from 1 to 3, and Y stands for a hydrogen atom, a hydroxy group, an alkoxy group or an amino group, wherein the amino group may be substituted with one or two Q groups and Y stands for a hydrogen atom when n=0;

wherein the at least one compound of formula (I) selected from 6-(methoxymethoxy) benzene-1,2,4-triamine; 6-(2-methoxyethoxy) benzene-1,2,4-triamine; 6-(2-ethoxyethoxy) benzene-1,2,4-triamine; and/or a physiologically compatible salt thereof.

\* \* \* \* \*